United States Patent
Ryu et al.

(10) Patent No.: US 10,526,282 B2
(45) Date of Patent: Jan. 7, 2020

(54) FLUORINE-BASED COMPOUND FOR BRANCHER, POLYMER USING SAME, AND POLYMER ELECTROLYTE MEMBRANE USING SAME

(71) Applicant: LG CHEM, LTD., Seoul (KR)

(72) Inventors: Hyun Woog Ryu, Daejeon (KR); Sehee Jung, Daejeon (KR); Joong Jin Han, Daejeon (KR); Yong Jin Jang, Daejeon (KR); Youngjea Kim, Daejeon (KR); Esder Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 228 days.

(21) Appl. No.: 15/515,007

(22) PCT Filed: Oct. 28, 2015

(86) PCT No.: PCT/KR2015/011462
§ 371 (c)(1),
(2) Date: Mar. 28, 2017

(87) PCT Pub. No.: WO2016/068605
PCT Pub. Date: May 6, 2016

(65) Prior Publication Data
US 2017/0226054 A1    Aug. 10, 2017

(30) Foreign Application Priority Data

Oct. 28, 2014  (KR) .................. 10-2014-0147787
Oct. 28, 2014  (KR) .................. 10-2014-0147791

(51) Int. Cl.
*C07C 323/09*  (2006.01)
*C08L 71/12*   (2006.01)
(Continued)

(52) U.S. Cl.
CPC ............. *C07C 323/09* (2013.01); *B01J 39/19* (2017.01); *C07C 43/275* (2013.01); *C07C 43/29* (2013.01);
(Continued)

(58) Field of Classification Search
CPC ....... H01M 2008/1095; H01M 8/1032; H01M 8/1025
See application file for complete search history.

(56) References Cited

U.S. PATENT DOCUMENTS

| 5,084,548 A | 1/1992 | Feiring et al. |
| 5,196,604 A | 3/1993 | Feiring et al. |

(Continued)

FOREIGN PATENT DOCUMENTS

| JP | 5-112648 A | 5/1993 |
| JP | 2013-218868 A | 10/2013 |

(Continued)

OTHER PUBLICATIONS

Petrova et al. (Journal of Fluorine Chemistry 98 (1999) 17-28).*
(Continued)

*Primary Examiner* — Olatunji A Godo
(74) *Attorney, Agent, or Firm* — Birch, Stewart, Kolasch & Birch, LLP

(57) ABSTRACT

The present specification relates to a fluorine-based compound for a brancher, a polymer using the same, a polymer electrolyte membrane using the same, a fuel cell using the same, and a redox flow battery including the same.

17 Claims, 4 Drawing Sheets

(51) Int. Cl.
*C08G 65/40* (2006.01)
*C07C 43/29* (2006.01)
*C08G 75/02* (2016.01)
*C07C 317/12* (2006.01)
*H01M 8/10* (2016.01)
*C07C 43/275* (2006.01)
*H01M 8/18* (2006.01)
*B01J 39/19* (2017.01)
*C08G 75/0245* (2016.01)
*C08G 75/12* (2016.01)
*H01M 8/1039* (2016.01)
*H01M 8/1018* (2016.01)

(52) U.S. Cl.
CPC ............ *C07C 317/12* (2013.01); *C08G 65/40* (2013.01); *C08G 75/02* (2013.01); *C08G 75/0245* (2013.01); *C08G 75/12* (2013.01); *C08L 71/12* (2013.01); *H01M 8/10* (2013.01); *H01M 8/1039* (2013.01); *H01M 8/18* (2013.01); *H01M 8/188* (2013.01); *C08G 2650/40* (2013.01); *C08G 2650/48* (2013.01); *H01M 2008/1095* (2013.01); *Y02E 60/528* (2013.01)

(56) References Cited

U.S. PATENT DOCUMENTS

| | | | |
|---|---|---|---|
| 2006/0003209 A1* | 1/2006 | Kim | C08J 5/2275 429/494 |
| 2006/0160960 A1* | 7/2006 | Chang | C08G 65/4056 525/344 |
| 2013/0184428 A1* | 7/2013 | Fedurco | B01D 67/0009 528/172 |
| 2013/0197110 A1 | 8/2013 | Fedurco | |
| 2013/0217851 A1 | 8/2013 | Fedurco et al. | |

FOREIGN PATENT DOCUMENTS

KR 10-2003-0076057 A 9/2003
KR 10-2017-0012982 A 2/2017

OTHER PUBLICATIONS

European Search Report for Appl. No. 15855925.2 dated Jun. 14, 2018.
Feiring, A.E., et al, "Fluorinated Poly(ether Sulfone)s", Journal of Polymer Science, Sep. 1, 1990, vol. 28, No. 10, pp. 2809-2819.
Buxton, M.W. et al, "Perfluoroaralkyl Ethers," J. Fluorine Chem., 1973, vol. 2, pp. 231-245.
International Search Report for PCT/KR2015/011462 dated Jan. 13, 2016.

* cited by examiner

[FIG. 1]
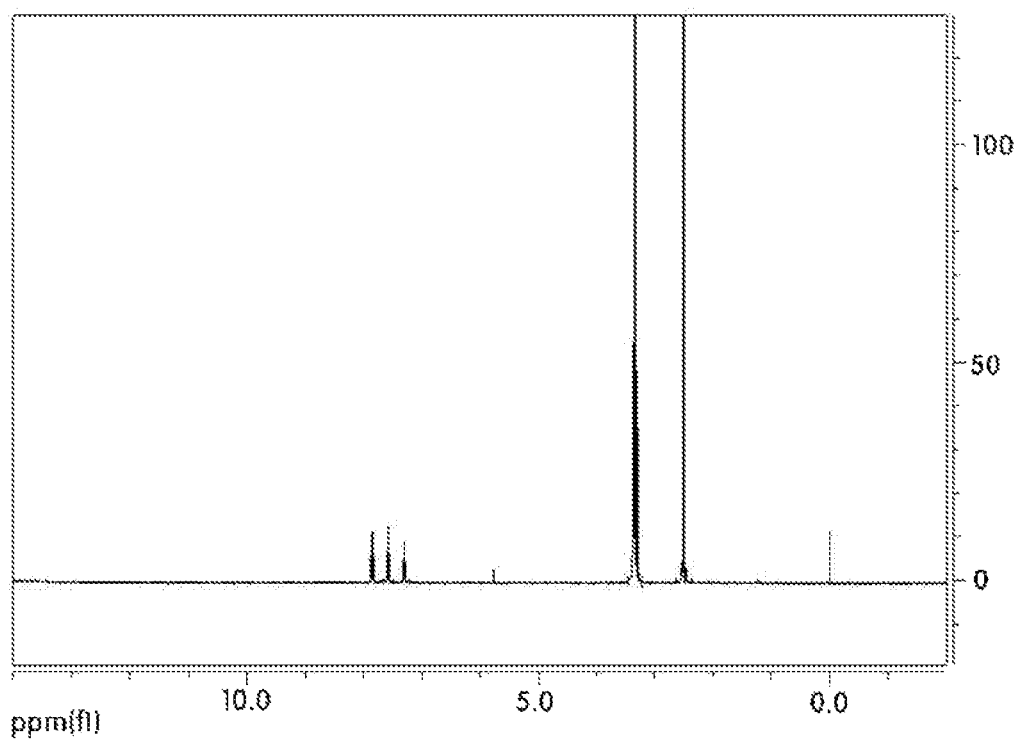

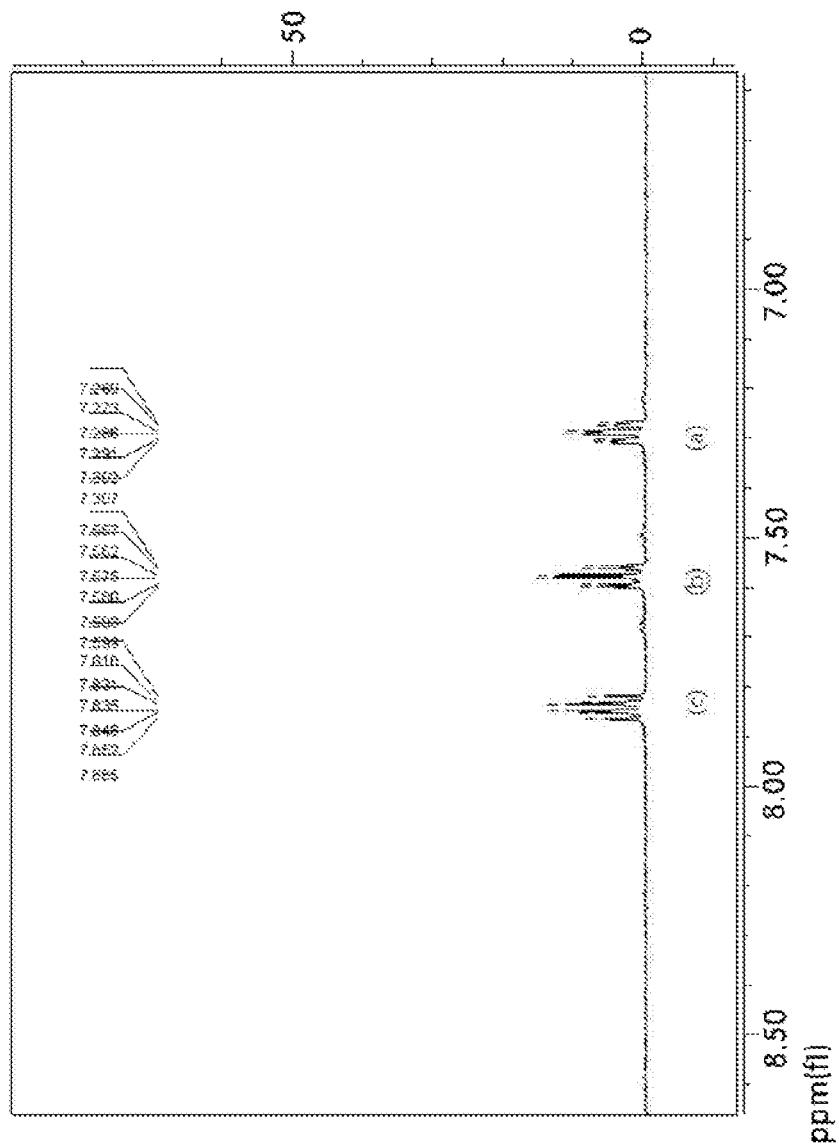
[FIG. 2]

[FIG. 3]
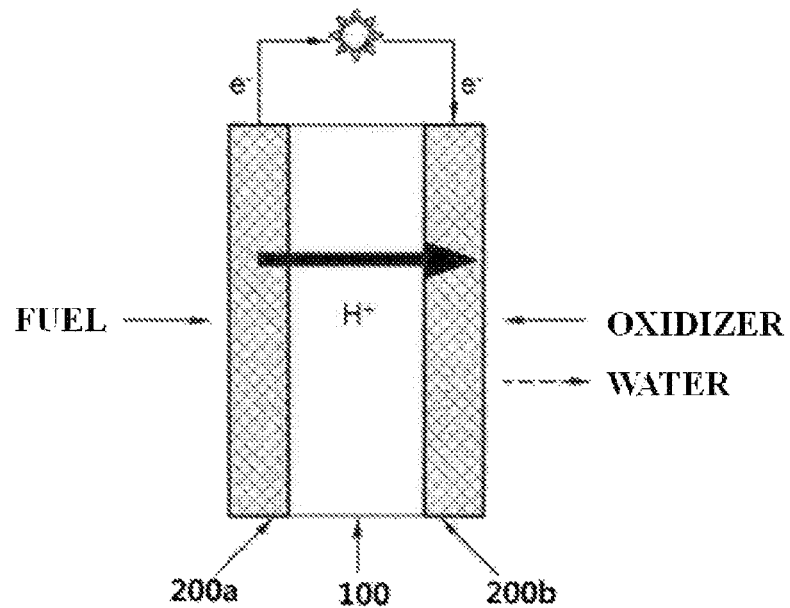
[FIG. 4]
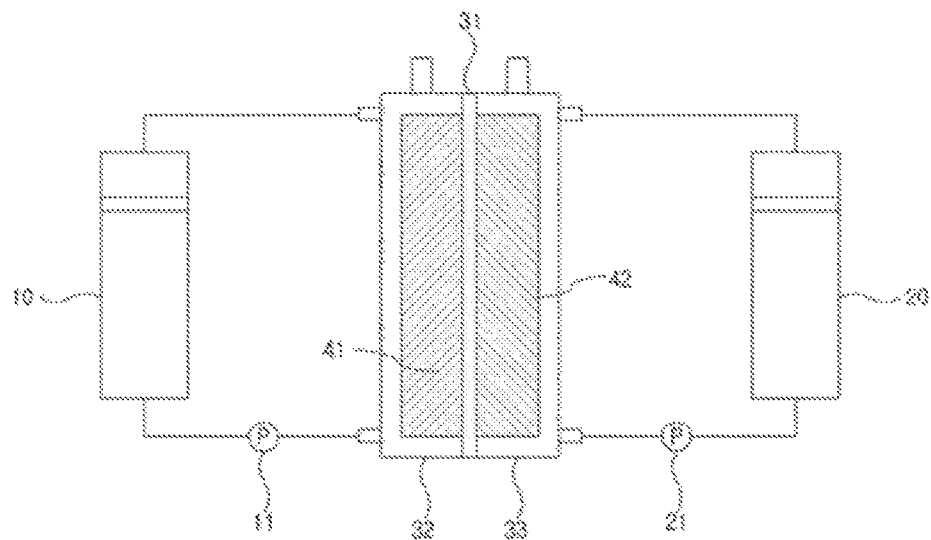

[FIG. 5]
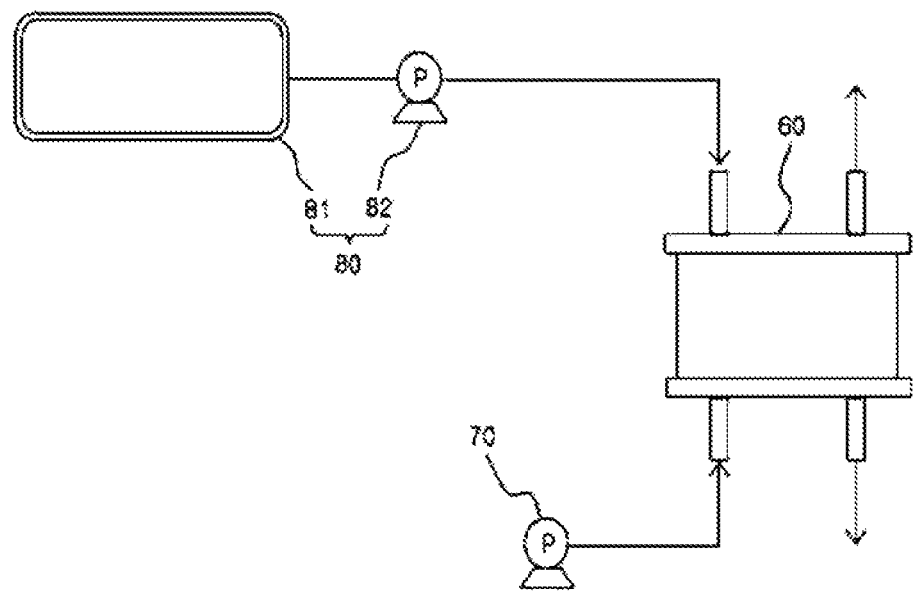

FLUORINE-BASED COMPOUND FOR BRANCHER, POLYMER USING SAME, AND POLYMER ELECTROLYTE MEMBRANE USING SAME

TECHNICAL FIELD

This application claims priority to and the benefits of Korean Patent Application No. 10-2014-0147787 and No. 10-2014-0147791, filed with the Korean Intellectual Property Office on Oct. 28, 2014, the entire contents of which are incorporated herein by reference.

The present specification relates to a fluorine-based compound for a brancher, a polymer using the same, a polymer electrolyte membrane using the same, a fuel cell including the same, and a redox flow battery including the same.

BACKGROUND ART

Polymers are compounds having a high molecular weight (polymer), and refer to compounds formed through polymerization of several low molecular weight compounds called monomers. Polymers may be divided into linear polymers, branched polymers, crosslinked polymer and the like depending on the chain structures and forms, and show big differences in physical and chemical properties depending on the structures.

Polymers have excellent mechanical strength considering their relatively light weight and have favorable processibility, and have been mainly used as materials forming structures, however, use of polymers as functional materials has recently emerged due to their excellent physical and chemical properties.

Typical examples thereof may include use as a polymer separator. A polymer separator means a polymer membrane having a function of separating materials rather than a simple thin membrane such as films. Specifically, polymers have been used as an electrolyte membrane capable of cation exchange in fuel cells, redox flow batteries and the like.

A fuel cell is an energy conversion device directly converting chemical energy of fuel into electric energy. In other words, a fuel cell employs a power generation method utilizing a fuel gas and an oxidizer, and using electrons generated during the oxidation and reduction reactions of these to produce power. A membrane-electrode assembly (MEA) of a fuel cell is a part where an electrochemical reaction of hydrogen and oxygen occurs, and is formed with a cathode, an anode and an electrolyte membrane, that is, an ion conductive electrolyte membrane.

A redox flow battery (oxidation-reduction flow battery) is a system charged and discharged by active materials included in a liquid electrolyte being oxidized and reduced, and is an electrochemical storage device directly storing chemical energy of the active materials as electric energy. A unit cell of the redox flow battery includes an electrode, an electrolyte and an ion-exchange membrane (electrolyte membrane).

Due to their high energy efficiency and environmental friendly properties of low contaminant emissions, fuel cells and redox flow batteries have been researched and developed as a next generation energy source.

One of core constituents in a fuel cell and a redox flow battery is a polymer electrolyte membrane capable of cation exchange, and properties of 1) excellent proton conductivity, 2) preventing electrolyte cross over, 3) high chemical resistance, 4) strengthening mechanical properties and/or 5) low swelling ratio are favorably required.

The polymer electrolyte membrane is divided into fluorine-based, partial fluorine-based, hydrocarbon-based and the like, and the partial fluorine-based polymer electrolyte membrane has excellent physical and chemical stability due to a fluorine-based main chain, and has an advantage of exhibiting high thermal stability. In addition, in the partial fluorine-based polymer electrolyte membrane, a cation transfer functional group is attached at the end of the fluorine-based chain as in the fluorine-based polymer electrolyte membrane, and therefore, advantages of both the hydrocarbon-based polymer electrolyte membrane and the fluorine-based polymer electrolyte membrane are capable of being obtained.

Researches on monomers used in polymer syntheses have been conducted in order to prepare a polymer membrane for a fuel cell and/or a redox flow battery having high durability and acid resistance. In addition, in order to increase the use of partial fluorine-based polymer electrolyte membranes, researches on partial fluorine-based polymer electrolyte membranes with enhanced proton conductivity, mechanical properties, physical and chemical properties and the like have been ongoing.

PRIOR ART DOCUMENTS

Patent Documents

Korean Patent Application Laid-Open Publication No. 2003-0076057

DISCLOSURE

Technical Problem

The present specification is directed to providing a fluorine-based compound for a brancher, a polymer using the same, a polymer electrolyte membrane using the same, a fuel cell including the same, and a redox flow battery including the same.

Technical Solution

One embodiment of the present specification provides a fluorine-based compound for a brancher, a polymer using the same, a polymer electrolyte membrane using the same, a fuel cell including the same, and a redox flow battery including the same.

[Chemical Formula 1]

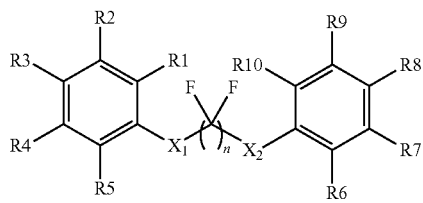

In Chemical Formula 1,

R1 to R10 are the same as or different from each other, and each independently hydrogen or a halogen group, two of R1 to R5 are a halogen group, two of R6 to R10 are a halogen group, $X_1$ and $X_2$ are the same as or different from each other, and each independently NR, O, S or $SO_2$, R is hydrogen; deuterium; or a substituted or unsubstituted alkyl group, and n is an integer of 1 to 6.

Another embodiment of the present specification provides a polymer including a monomer derived from the compound for a brancher represented by Chemical Formula 1 as a brancher.

Still another embodiment of the present specification provides a membrane-electrode assembly including a positive electrode; a negative electrode; and an electrolyte membrane provided between the positive electrode and the negative electrode, wherein the electrolyte membrane is the polymer electrolyte membrane.

Yet another embodiment of the present specification provides a polymer electrolyte-type fuel cell including a stack including two or more of the membrane-electrode assemblies and a bipolar plate provided between the membrane-electrode assemblies; a fuel supplying unit supplying fuel to the stack; and an oxidizer supplying unit supplying an oxidizer to the stack.

Still yet another embodiment of the present specification provides a redox flow battery including a positive electrode cell including a positive electrode and a positive electrode liquid electrolyte; a negative electrode cell including a negative electrode and a negative electrode liquid electrolyte; and the polymer electrolyte membrane provided between the positive electrode cell and the negative electrode cell.

Advantageous Effects

A polymer synthesized using a compound for a brancher according to one embodiment of the present specification has excellent durability and acid resistance.

In addition, a polymer according to one embodiment of the present specification has a high molecular weight by including a monomer derived from a compound having a plurality of reaction sites.

A polymer electrolyte membrane according to one embodiment of the present specification has excellent durability and acid resistance. In other words, a polymer electrolyte membrane having excellent physical and chemical stability can be provided.

A polymer electrolyte membrane according to one embodiment of the present specification has excellent proton conductivity.

A fuel cell and/or a redox flow battery according to one embodiment of the present specification including the polymer electrolyte membrane exhibit superior performance.

DESCRIPTION OF DRAWINGS

FIG. 1 and FIG. 2 are graphs showing NMR analysis results of a compound for a brancher represented by Chemical Formula 1 prepared according to a synthesis example.

FIG. 3 is a schematic diagram showing a principle of electricity generation of a fuel cell.

FIG. 4 is a diagram schematically illustrating one embodiment of a redox flow battery.

FIG. 5 is a diagram schematically illustrating one embodiment of a fuel cell.

REFERENCE NUMERAL

100: Electrolyte Membrane
200*a*: Positive Electrode
200*b*: Negative Electrode
10, 20: Tank
11, 21: Pump
31: Electrolyte Membrane
32: Positive Electrode Cell
33: Negative Electrode Cell
41: Positive Electrode Liquid Electrolyte
42: Negative Electrode Liquid Electrolyte
60: Stack
70: Oxidizer Supplying Unit
80: Fuel Supplying Unit
81: Fuel Tank
82: Pump

MODE FOR DISCLOSURE

Hereinafter, the present specification will be described in more detail.

In the present specification, the term "substituted or unsubstituted" means being substituted with one or more substituents selected from the group consisting of deuterium; a halogen group; an alkoxy group; an alkyl group; and a phenyl group, or having no substituents. The alkyl group or the phenyl group may be additionally substituted.

In the present specification, a "monomer" means a structure in which a compound is included in a divalent or higher form in a polymer through a polymerization reaction.

In the present specification, a "brancher" means, as a compound having three or more reactive substituents, a compound enabling to form a branched polymer, that is, a polymer structure including a main chain, a branch point and a side chain linked to the main chain at the branch point when included as a monomer of a polymer.

A compound for a brancher represented by Chemical Formula 1 according to one embodiment of the present specification is substituted with a halogen group on at least four positions as described above, and positions of the halogen group substitutions are not particularly limited. In other words, the monomer may have reaction sites at various positions, and accordingly, when used as a monomer in polymer synthesis, flexibility of hydrophilic monomers, hydrophobic monomers and/or blocks increases, and effects of molecular weight increase and/or physical property enhancement of a final polymer may be obtained.

According to one embodiment of the present specification, the compound for a brancher represented by Chemical Formula 1 may include a halogen group at a specific position of ortho, meta or para. Specifically, a halogen group may be located at a 2, 3 or 4 position of the benzene ring. Using a fluorine-based chain having an electron withdrawing property as a monomer in polymer synthesis is effective in increasing polymerization reactivity since the fluorine-based chain further increases reactivity at 2 and 4 positions of the benzene ring at which halogen groups are present.

According to one embodiment of the present specification, R3, R5, R6 and R8 are a halogen group.

According to one embodiment of the present specification, R3, R5, R6 and R8 are each independently fluorine (F), chlorine (Cl) or bromine (Br).

According to one embodiment of the present specification, R3, R5, R6 and R8 are each independently fluorine (F) or chlorine (Cl).

According to one embodiment of the present specification, R3, R5, R6 and R8 are a halogen group, and R1, R2, R4, R7, R9 and R10 are hydrogen.

According to one embodiment of the present specification, R2, R5, R6 and R8 are a halogen group.

According to one embodiment of the present specification, R2, R5, R6 and R8 are each independently fluorine (F), chlorine (Cl) or bromine (Br).

According to one embodiment of the present specification, R2, R5, R6 and R8 are each independently fluorine (F) or chlorine (Cl).

According to one embodiment of the present specification, R2, R5, R6 and R9 are a halogen group.

According to one embodiment of the present specification, R2, R5, R6 and R9 are each independently fluorine (F), chlorine (Cl) or bromine (Br).

According to one embodiment of the present specification, R2, R5, R6 and R9 are each independently fluorine (F) or chlorine (Cl).

According to one embodiment of the present specification, R3, R4, R6 and R8 are a halogen group.

According to one embodiment of the present specification, R3, R4, R6 and R8 are each independently fluorine (F), chlorine (Cl) or bromine (Br).

According to one embodiment of the present specification, R3, R4, R6 and R8 are each independently fluorine (F) or chlorine (Cl).

According to one embodiment of the present specification, R3, R4, R7 and R8 are a halogen group.

According to one embodiment of the present specification, R3, R4, R7 and R8 are each independently fluorine (F), chlorine (Cl) or bromine (Br).

According to one embodiment of the present specification, R3, R4, R7 and R8 are each independently fluorine (F) or chlorine (Cl).

According to one embodiment of the present specification, R3, R4, R6 and R9 are a halogen group.

According to one embodiment of the present specification, R3, R4, R6 and R9 are each independently fluorine (F), chlorine (Cl) or bromine (Br).

According to one embodiment of the present specification, R3, R4, R6 and R9 are each independently fluorine (F) or chlorine (Cl).

According to one embodiment of the present specification, R2, R3, R6 and R7 are a halogen group.

According to one embodiment of the present specification, R2, R3, R6 and R7 are each independently fluorine (F), chlorine (Cl) or bromine (Br).

According to one embodiment of the present specification, R2, R3, R6 and R7 are each independently fluorine (F) or chlorine (Cl).

According to one embodiment of the present specification, R3, R5, R6 and R9 are a halogen group.

According to one embodiment of the present specification, R3, R5, R6 and R9 are each independently fluorine (F), chlorine (Cl) or bromine (Br).

According to one embodiment of the present specification, R3, R5, R6 and R9 are each independently fluorine (F) or chlorine (Cl).

According to one embodiment of the present specification, R4, R5, R7 and R9 are a halogen group.

According to one embodiment of the present specification, R4, R5, R7 and R9 are each independently fluorine (F), chlorine (Cl) or bromine (Br).

According to one embodiment of the present specification, R4, R5, R7 and R9 are each independently fluorine (F) or chlorine (Cl).

According to one embodiment of the present specification, R3, R5, R7 and R8 are a halogen group.

According to one embodiment of the present specification, R3, R5, R7 and R8 are each independently fluorine (F), chlorine (Cl) or bromine (Br).

According to one embodiment of the present specification, R3, R5, R7 and R8 are each independently fluorine (F) or chlorine (Cl).

According to one embodiment of the present specification, the halogen group is fluorine or chlorine. Fluorine or chlorine has high electronegativity increasing electrophilicity of parts substituted with fluorine or chlorine, and accordingly, has an advantageous effect of increasing reactivity in nucleophilic substitution.

In the compound for a brancher represented by Chemical Formula 1, two benzene rings are linked through a linker, and the linker employs a structure having an alkyl group substituted with fluorine between two heteroatoms. When the compound for a brancher represented by Chemical Formula 1 is included in a polymer membrane, fluorine with high electronegativity located at the linker favorably attracts electrons and thereby facilitates hydrogen ion migration, and has an advantage of strengthening a structure of the polymer membrane. Fluorine that has highest electronegativity among halogen groups is included, and therefore, the above-mentioned advantage may be maximized. Furthermore, the polymer membrane including the compound for a brancher represented by Chemical Formula 1 has an advantage of exhibiting excellent durability.

The compound for a brancher represented by Chemical Formula 1 has a linker including two heteroatoms between the benzene rings. Specifically, the heteroatoms are NR, O, S or $SO_2$, and R has the same definition as above. By introducing the above-mentioned heteroatoms having excellent acid resistance, particularly, introducing NR, S or $SO_2$, a polymer membrane including the compound for a brancher represented by Chemical Formula 1 has an advantage of exhibiting excellent acid resistance.

According to one embodiment of the present specification, R may be a substituted or unsubstituted alkyl group having 1 to 12 carbon atoms.

According to one embodiment of the present specification, R may be a substituted or unsubstituted alkyl group having 1 to 6 carbon atoms.

According to one embodiment of the present specification, $X_1$ and $X_2$ are the same as or different from each other, and each independently S or $SO_2$. When $X_1$ and $X_2$ are S or $SO_2$, a polymer membrane including the same has an advantage of enhancing durability. This is due to chemical stability, a property of not readily decomposed, of S or $SO_2$.

The compound for a brancher represented by Chemical Formula 1 may have flexibility by including a fluorocarbon-based chain between the two benzene rings together with the heteroatoms. As the length of the fluorocarbon-based chain increases, flexibility increases. n, which means a number of repetition of the fluorocarbon-based chain, is an integer of 1 to 6 as described above. When n is greater than 6, there may be a problem of hydrophilic blocks being excessively formed in a polymer electrolyte membrane including a polymer including the same. In other words, when n is 6 or less, there is an advantage of enhancing polymer electrolyte membrane performance since a proper phase separation phenomenon occurs.

In addition, by adjusting the length of the fluorocarbon-based chain, steric hindrance that may occur during the polymerization may be suppressed, which finally leads to an advantage of increasing the degree of polymerization.

According to one embodiment of the present specification, n is 2, 4 or 6.

According to one embodiment of the present specification, n is 3 or more.

According to one embodiment of the present specification, n is 4 or more.

According to one embodiment of the present specification, n is 5 or more.

According to one embodiment of the present specification, n is 6.

In addition, the compound for a brancher represented by Chemical Formula 1 has a 3-dimensional structure and thereby has a wider polymerization space compared to a flat structure, and accordingly, has an advantage of obtaining a polymer having a high molecular weight when used in polymer polymerization.

According to one embodiment of the present specification, the compound for a brancher represented by Chemical Formula 1 may be any one selected from the following structures.

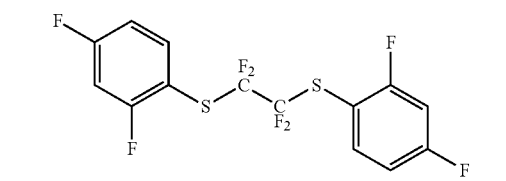

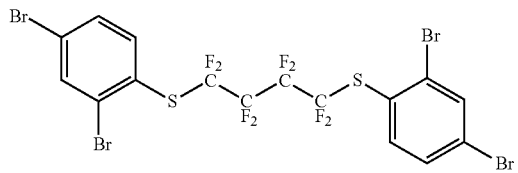

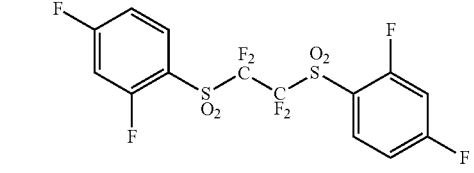

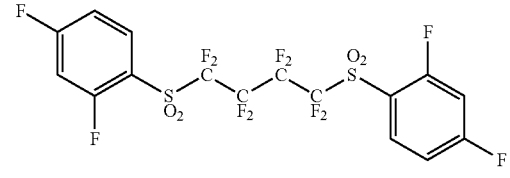

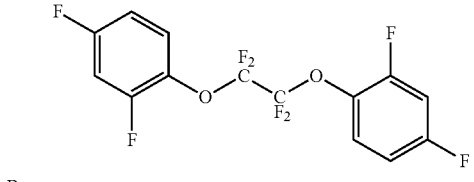

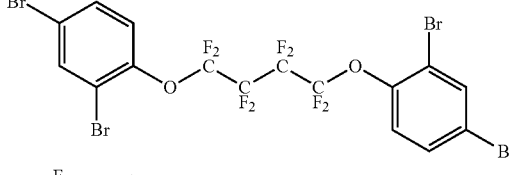

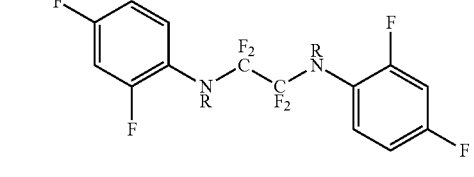

-continued

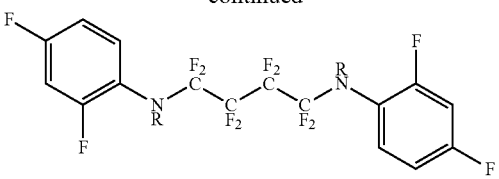

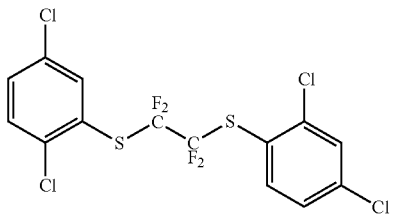

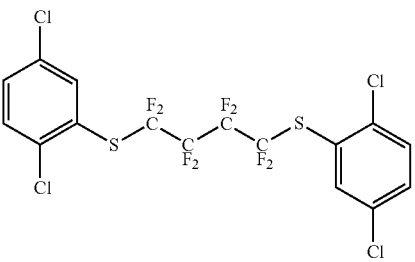

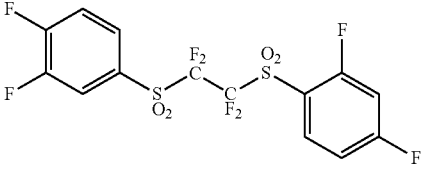

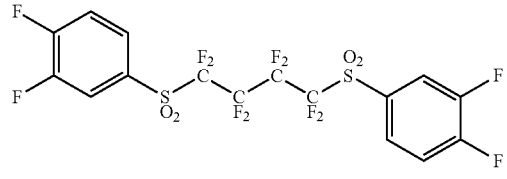

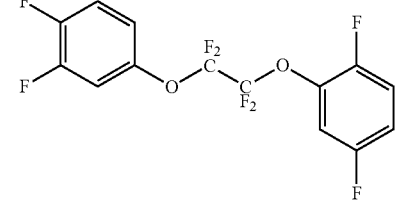

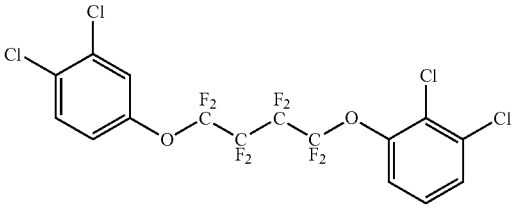

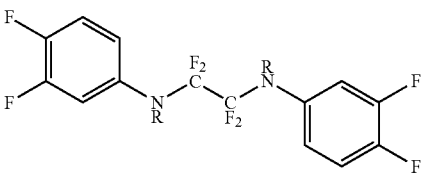

-continued

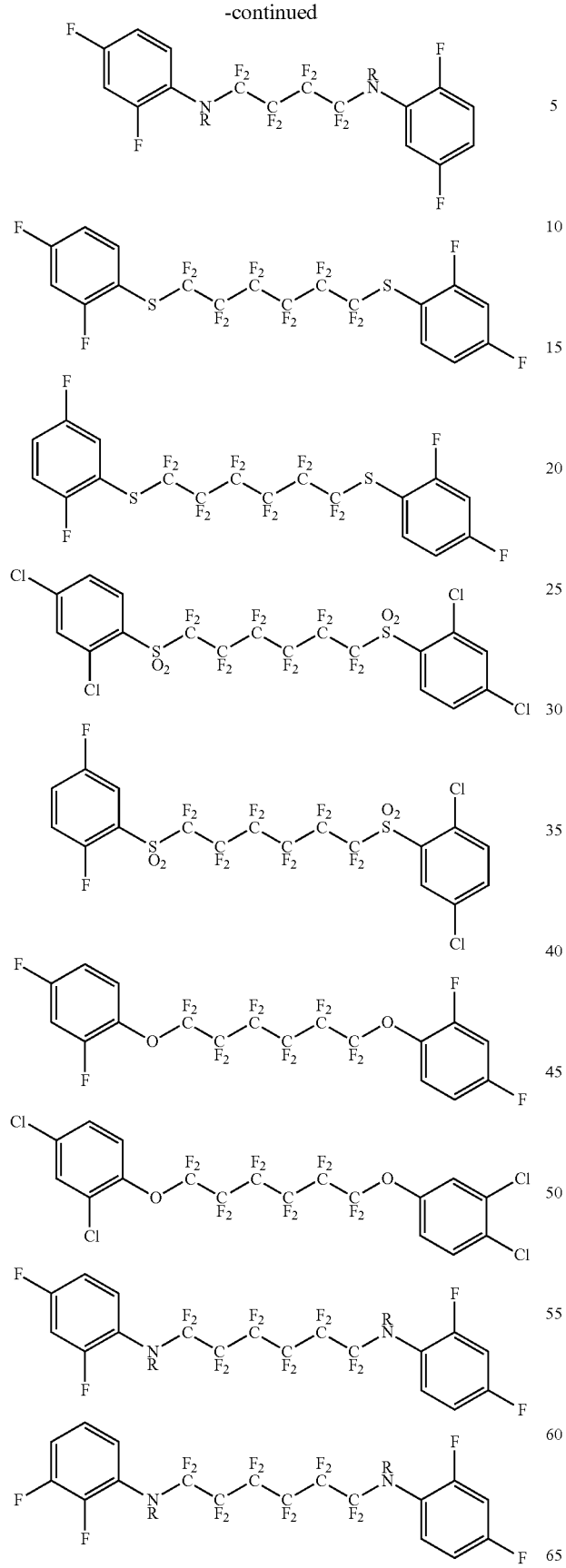

The compound for a brancher represented by Chemical Formula 1 may be prepared based on a preparation example to be described below. In addition, in the preparation example to be described below, various compounds represented by Chemical Formula 1 may be obtained by changing the elements corresponding to $X_1$ and $X_2$ to other elements instead of sulfur, and by controlling n, compounds for a brancher represented by Chemical Formula 1 having varied flexibility may be obtained.

When synthesizing a polymer using the compound for a brancher represented by Chemical Formula 1, effects described above may be obtained. In this case, the polymer may include monomers other than the compound for a brancher represented by Chemical Formula 1.

Specifically, a monomer derived from the compound for a brancher represented by Chemical Formula 1 may have structures as follows. However, the structures are not limited to the following structures.

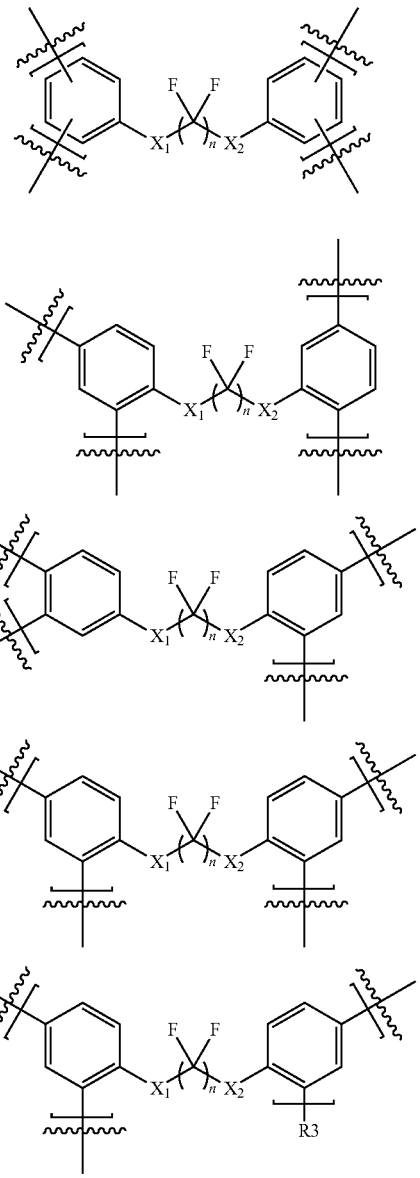

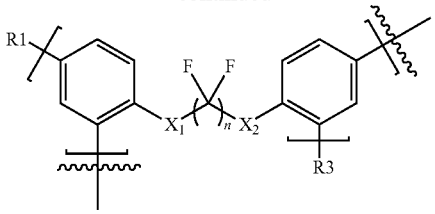

According to one embodiment of the present specification, the monomer is a monomer for a brancher. As described above, a brancher performs a role of linking or crosslinking a polymer chain. Depending on the number of repeating units of a monomer derived from the compound for a brancher represented by Chemical Formula 1 used as a brancher, branches may be formed on the chain, or the chains may be crosslinked to each other to form a mesh-type structure.

Separators for a fuel cell and/or a redox flow battery having been used in the art have had a problem of radical attacks during polymerization or bond breakage caused by sulfuric acid electrolyte during separator tests. As one example, typical branchers that have been used in the art have had a problem of bond breakage of a ketone group located on the main chain of the brancher caused by radicals that may be generated during a polymerization reaction. In other words, there has been a problem in that thermal stability and chemical stability decline.

Using the monomer included in the polymer according to one embodiment of the present specification as a brancher has an advantage in that physical stability and chemical stability are enhanced by the fluorine-based group located between the two benzene rings. Specific descriptions thereon are as follows.

In the monomer derived from the compound for a brancher represented by Chemical Formula 1 included in the polymer according to one embodiment of the present specification, two benzene rings are linked through a linker, and the linker employs a structure having a fluorine-substituted alkyl group between two heteroatoms. When the polymer is included in the polymer electrolyte membrane, fluorine with high electronegativity located on the linker favorably withdraws electrons and may facilitate hydrogen ion migration, and has an advantage of strengthening a structure of the polymer electrolyte membrane. Fluorine that has highest electronegativity among halogen groups is included, and therefore, the above-mentioned advantage may be maximized. Moreover, the polymer membrane including the compound for a brancher represented by Chemical Formula 1 has an advantage of exhibiting excellent durability.

The monomer derived from the compound for a brancher represented by Chemical Formula 1 included in the polymer according to one embodiment of the present specification includes two benzene rings, and each benzene ring is substituted with a halogen group on at least two positions. In other words, the monomer is substituted with a halogen group on at least four positions. As a result, the monomer has four reaction sites and has an advantage of obtaining a polymer having a high molecular weight.

As described above, the monomer derived from the compound for a brancher represented by Chemical Formula 1 included in the polymer according to one embodiment of the present specification is substituted with a halogen group on at least four positions, and positions of the halogen group substitutions are not particularly limited. In other words, the monomer may have reaction sites at various positions, and as a result, flexibility of hydrophilic monomers, hydrophobic monomers and/or blocks increases leading to an effect of molecular weight increase and/or physical property enhancement of a final polymer.

In addition, when using the monomer derived from the compound for a brancher represented by Chemical Formula 1 as a brancher, length, distribution, location, number and the like of the brancher may be controlled in the polymer skeleton, and in this case, there is an advantage in that a thin film is capable of being effectively prepared since physical and chemical properties of a polymer electrolyte membrane do not decline.

The monomer included in the polymer according to one embodiment of the present specification has a linker including two heteroatoms between the two benzene rings. Specifically, the heteroatoms are NR, O, S or $SO_2$, and R has the same definition as above. Particularly, the heteroatoms being NR, S or $SO_2$ has an advantage in that a polymer electrolyte membrane including the polymer according to one embodiment of the present specification has excellent acid resistance by introducing the heteroatom having excellent acid resistance.

According to one embodiment of the present specification, $X_1$ and $X_2$ are the same as or different from each other, and each independently S or $SO_2$. When $X_1$ and $X_2$ are S or $SO_2$, a polymer electrolyte membrane including the same has an advantage of enhancing durability. This is caused by chemical stability, a property that is not readily decomposed, of S or $SO_2$.

The monomer included in the polymer according to one embodiment of the present specification has an advantage of providing flexibility by adding a fluorocarbon-based chain between the two benzene rings together with the heteroatom. As the length of the fluorocarbon-based chain increases, flexibility increases. In addition, by controlling the length of the fluorocarbon-based chain, steric hindrance that may occur during the polymerization may be suppressed, which finally leads to an advantage of enhancing the degree of polymerization.

Moreover, the compound for a brancher represented by Chemical Formula 1 has a 3-dimensional structure and thereby has wider polymerization space compared to a flat structure, and therefore, when used in polymer polymerization, has an advantage of obtaining a polymer having a high molecular weight. In other words, the polymer according to one embodiment of the present specification has an advantage of having a high molecular weight by including the monomer derived from the compound for a brancher represented by Chemical Formula 1.

A polymer membrane including the polymer prepared using the compound for a brancher represented by Chemical Formula 1 is capable of exhibiting the above-described effects. The polymer membrane may mean a membrane capable of exchanging ions, and may be utilized in fuel cells, redox flow batteries and the like.

The compound for a brancher represented by Chemical Formula 1 may be prepared based on a preparation example to be described below. According to one embodiment, the compound for a brancher represented by Chemical Formula 1 may be prepared in a manner as in the following Reaction Formula 1.

[Reaction Formula 1]

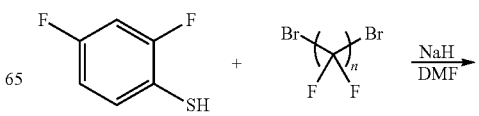

-continued

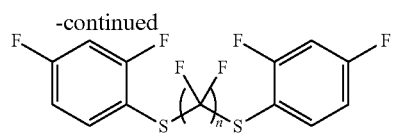

By changing the position of fluorine substitution of reaction materials in Reaction Formula 1, compounds for a brancher represented by Chemical Formula 1 having fluorine substituted at varied positions may be obtained.

According to one embodiment of the present specification, the polymer may include additional co-monomers. As the additional co-monomer, those known in the art may be used. Herein, one, two or more types of co-monomers may be used.

Examples of the co-monomer may include monomers forming perfluorosulfonic acid polymers, hydrocarbon-based polymers, polyimide, polyvinylidene fluoride, polyether sulfone, polyphenylene sulfide, polyphenylene oxide, polyphosphazene, polyethylene naphthalate, polyester, doped polybenzimidazole, polyetherketone, polysulfone, acids thereof, or bases thereof.

According to one embodiment of the present specification, content of the additional co-monomer in the polymer may be greater than 0% by weight and less than or equal to 95% by weight.

According to another embodiment, the monomer derived from the compound for a brancher represented by Chemical Formula 1 may be included in the polymer in greater than or equal to 0.001% by weight and less than or equal to 10% by weight with respect to the total weight of the polymer. When the monomer derived from the compound for a brancher represented by Chemical Formula 1 is included in 0.001% by weight or greater as a brancher, the brancher sufficiently increases the degree of crosslinking of the polymer obtaining an effect of physical property changes in the final polymer, and when included in 10% by weight or less, possibility of the generation of the residual brancher that has not participated in the reaction decreases in the polymer, and the terminal group may be designed as a hydroxyl group (—OH) when polymerizing the hydrophobic part, which finally leads to an advantage of polymerizing a target block-type copolymer.

The polymer including the monomer derived from the compound for a brancher represented by Chemical Formula 1 is preferably a block-type copolymer. The polymer may be synthesized using, for example, a condensation polymerization reaction bonding through a halogen group of the monomer being released as HF, HCl or the like by the reaction thereof.

According to one embodiment of the present specification, the polymer is a block-type copolymer including hydrophilic blocks and hydrophobic blocks.

According to one embodiment of the present specification, the monomer derived from the compound for a brancher represented by Chemical Formula 1 may be located between the hydrophilic blocks, between the hydrophobic blocks or between the hydrophilic block and the hydrophobic block.

The "hydrophilic block" of the present specification means a block having an ion-exchange group as a functional group. Herein, the functional group may be at least any one selected from the group consisting of —SO$_3$H, —SO$_3^-$M$^+$, —COOH, —COO$^-$M$^+$, —PO$_3$H$_2$, —PO$_3$H$^-$M$^+$ and —PO$_3^{2-}$2M$^+$. Herein, M may be a metallic element. In other words, the functional group may be hydrophilic.

The "block having an ion-exchange group" of the present specification means a block including an average of 0.5 or more ion-exchange groups when representing as the number of ion-exchange groups per one structure unit forming the corresponding block, and including an average of 1.0 or more ion-exchange groups per one structure unit is more preferred.

The "hydrophobic block" of the present specification means the polymer block that does not substantially include an ion-exchange group.

The "block that does not substantially include an ion-exchange group" of the present specification means a block including an average of less than 0.1 ion-exchange groups when representing as the number of ion-exchange groups per one structure unit forming the corresponding block, and including an average of 0.05 or less is more preferred, and a block that does not include an ion-exchange group at all is even more preferred.

Meanwhile, in the present specification, the "block-type copolymer" is a concept including, in addition to a copolymerization-style copolymer in which hydrophilic blocks and hydrophobic blocks form a main chain structure, a copolymerization-style copolymer of graft polymerization in which blocks on one side form a main chain structure, and blocks on the other side form a side chain structure. Meanwhile, the polymer used in the present specification is not limited to the block-type copolymer described above, and polymers including a fluorine-based element may also be used. Herein, the polymer including a fluorine-based element may also include a functional group, and the functional group may be hydrophilic. For example, the functional group may be at least any one selected from the group consisting of —SO$_3$H, —SO$_3^-$M$^+$, —COOH, —COO$^-$M$^+$, —PO$_3$H$_2$, —PO$_3$H$^-$M$^+$ and —PO$_3^{2-}$2M$^+$. Herein, M may be a metallic element.

According to one embodiment of the present specification, the block-type copolymer is a copolymer including a repeating unit of the following Chemical Formula A, a repeating unit of the following Chemical Formula B, and the monomer according to one embodiment of the present specification as a brancher:

[Chemical Formula A]

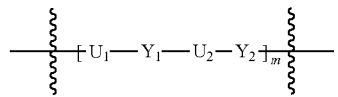

[Chemical Formula B]

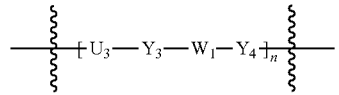

In Chemical Formula A and Chemical Formula B,

Y$_1$ to Y$_4$ are the same as or different from each other, and each independently —O—, —S— or —SO$_2$—, U$_1$ and U$_2$ are the same as or different from each other, and each independently represented by any one of the following Chemical Formula 2 to Chemical Formula 4,

[Chemical Formula 2]

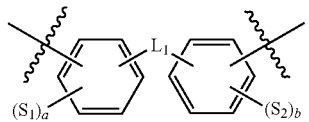

[Chemical Formula 3]

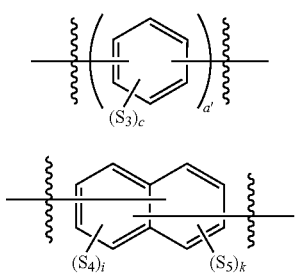

[Chemical Formula 4]

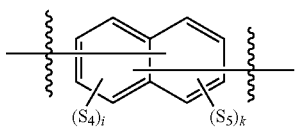

In Chemical Formula 2 to Chemical Formula 4, $L_1$ is any one of direct linking, —$CZ_1Z_2$—, —CO—, —O—, —S—, —$SO_2$—, —$SiZ_1Z_2$— and a substituted or unsubstituted fluorenyl group, $Z_1$ and $Z_2$ are the same as or different from each other, and each independently any one of hydrogen, an alkyl group, a trifluoromethyl group (—$CF_3$) and a phenyl group, $S_1$ to $S_5$ are the same as or different from each other, and each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heteroaryl group, a, b and c are the same as or different from each other, and each independently an integer of greater than or equal to 0 and less than or equal to 4, i and k are the same as or different from each other, and each independently an integer of greater than or equal to 0 and less than or equal to 3, a' is an integer of greater than or equal to 1 and less than or equal to 1000, in Chemical Formula B, $W_1$ is represented by any one of the following Chemical Formula 5 to Chemical Formula 7,

[Chemical Formula 5]

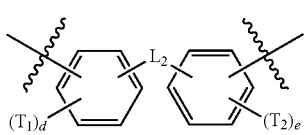

[Chemical Formula 6]

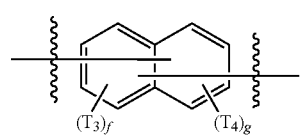

[Chemical Formula 7]

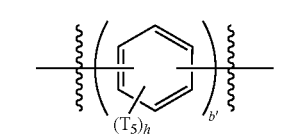

In Chemical Formulae 5 to 7, $L_2$ is any one selected from direct linking, —$CZ_3Z_4$—, —CO—, —O—, —S—, —$SO_2$—, —$SiZ_3Z_4$—, and a substituted or unsubstituted fluorenyl group, $Z_3$ and $Z_4$ are the same as or different from each other, and each independently any one of hydrogen, an alkyl group, a trifluoromethyl group (—$CF_3$) and a phenyl group, d, e, and h are the same as or different from each other, and each independently an integer of greater than or equal to 0 and less than or equal to 4, f and g are the same as or different from each other, and each independently an integer of greater than or equal to 0 and less than or equal to 3, b' is an integer of greater than or equal to 1 and less than or equal to 1000, $T_1$ to $T_5$ are the same as or different from each other, and each independently, at least one thereof is —$SO_3H$, —$SO_3^-M^+$, —COOH, —$COO^-M^+$, —$PO_3H_2$, —$PO_3H^-M^+$ or —$PO_3^{2-}M^+$, M is a group 1 element, and the rest are the same as or different from each other, and each independently hydrogen; deuterium; a halogen group; a cyano group; a nitrile group; a nitro group; a hydroxyl group; a substituted or unsubstituted alkyl group; a substituted or unsubstituted cycloalkyl group; a substituted or unsubstituted alkoxy group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heteroaryl group, in Chemical Formula B, $U_3$ is represented by any one of Chemical Formulae 2 to 7, m and n mean the number of repeating units, 1≤m≤500, 1≤n≤500, and the number of the monomer repeating units according to one embodiment of the present specification included as a brancher is greater than or equal to 1 and less than or equal to 300.

Particularly, when the number of repeating units is 10 or more in an ion transfer resin introducing the brancher, the degree of crosslinking between hydrophilic parts and hydrophobic parts in the polymer is sufficient, and polymers having a high molecular weight may be obtained, and as a result, sufficient impact strength may be obtained. In addition, there is an advantage in that physical properties of the resin are superior since ion transfer channels are favorably formed.

In addition, when the number of repeating units is 200 or more in an ion transfer resin introducing the brancher, the ion transfer resin is physically stable and ion transfer channels are favorably formed, which resultantly leads to an advantage of conductivity increase.

According to one embodiment of the present specification, the monomer derived from the compound for a brancher represented by Chemical Formula 1 is included in greater than or equal to 0.001% by weight and less than or equal to 10% by weight with respect to the total weight of the polymer.

When the brancher is used in 0.001% by weight or greater, the brancher sufficiently increases the degree of crosslinking of the polymer, and effects of physical property changes may be obtained in the final polymer, and when used in 10% by weight or less, the residual brancher that has not participated in the reaction is less likely to be produced in the polymer, and accordingly, the terminal group may be designed as a hydroxyl group (—OH) form during the hydrophobic part polymerization, which finally leads to an advantage of polymerizing a target block-type copolymer.

According to one embodiment of the present specification, $U_1$, $U_2$ and $U_3$ are the same as or different from each other, and each independently any one selected from the following structural formulae.

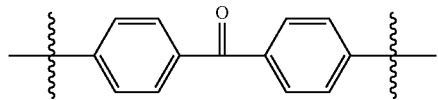

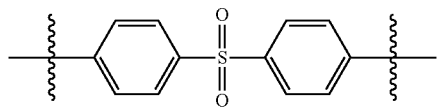

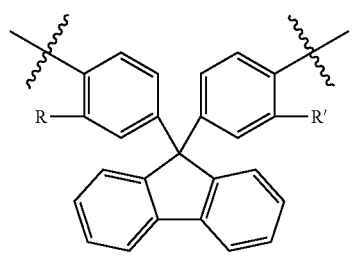

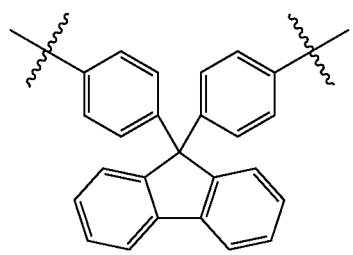

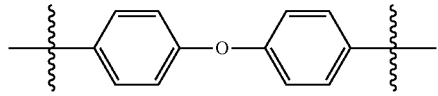

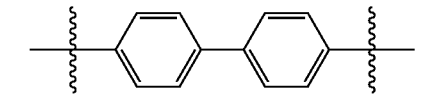

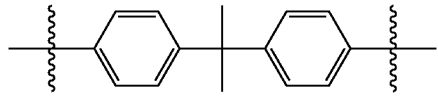

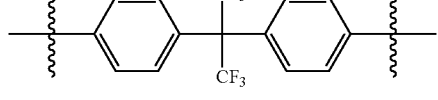

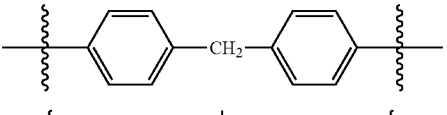

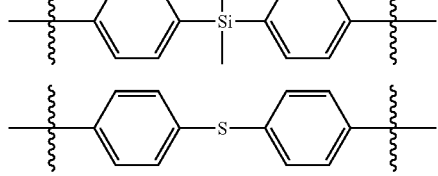

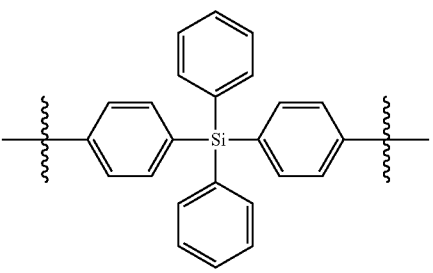

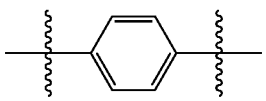

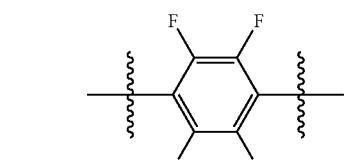

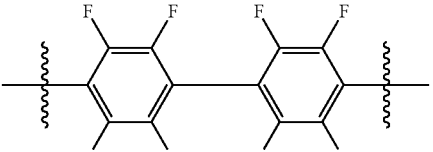

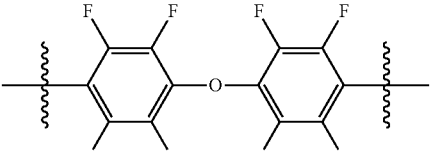

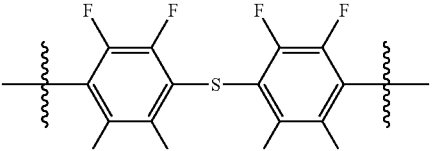

In the structural formulae, R and R' are each independently —$NO_2$ or —$CF_3$.

According to another embodiment, $W_1$ is any one selected from the following structural formulae.

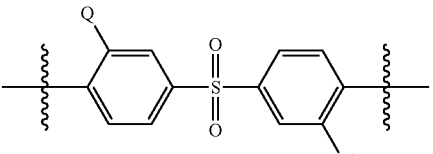

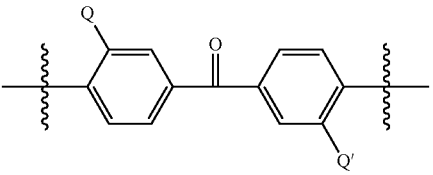

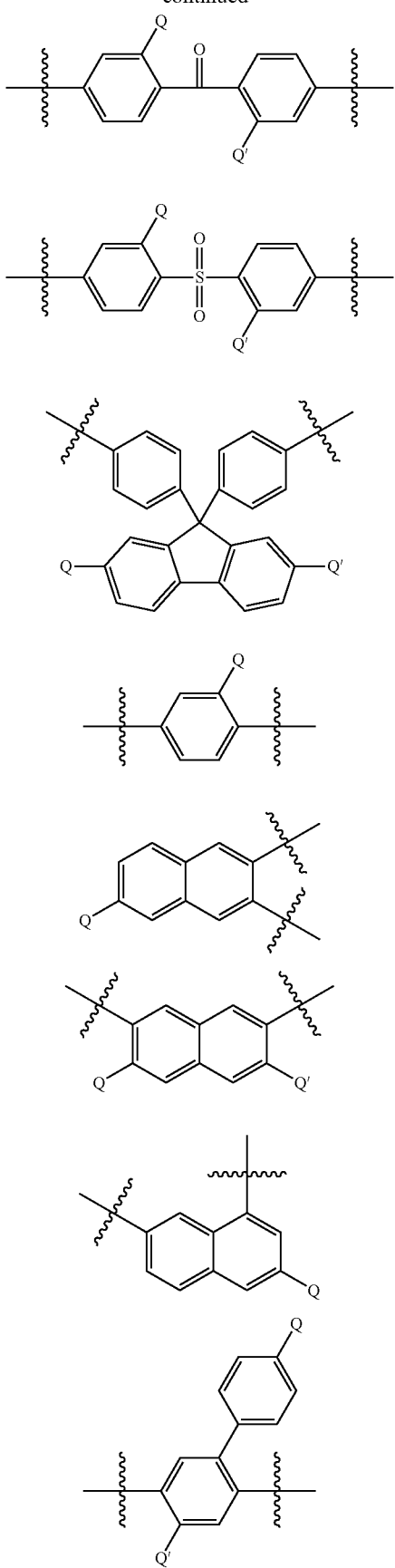
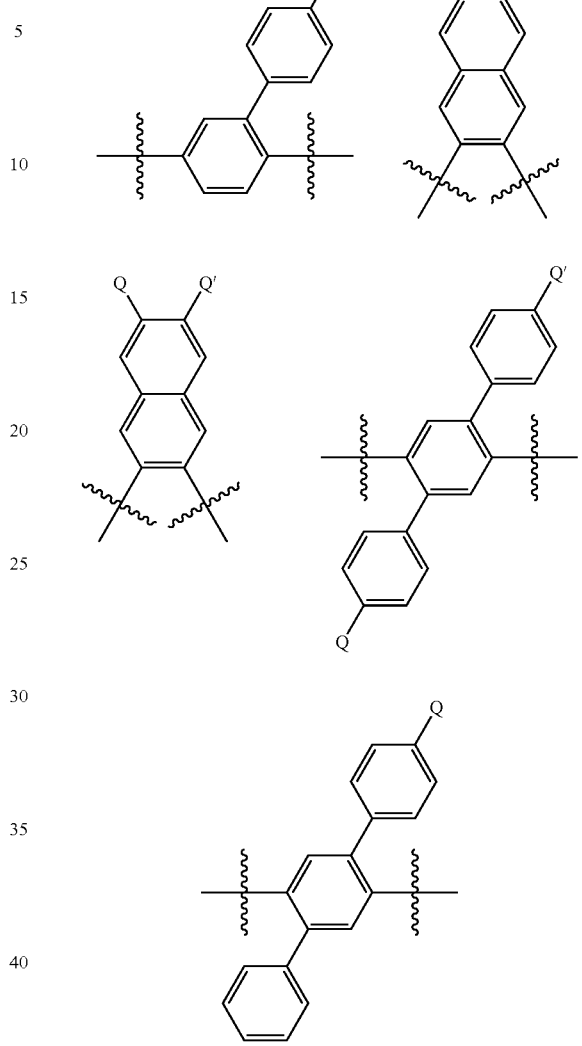
In the structural formulae, Q and Q' are each independently —SO$_3$H, —SO$_3^-$M$^+$, —COOH, —COO$^-$M$^+$, —PO$_3$H$_2$, —PO$_3$H$^-$M$^+$ or —PO$_3^{2-}$2M$^+$, and M is a group 1 metal.
According to one embodiment of the present specification, W$_1$ is any one selected from the following structural formulae.
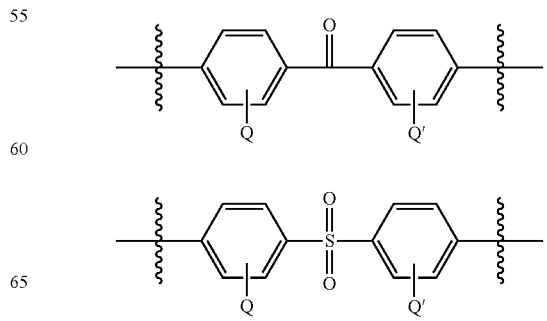

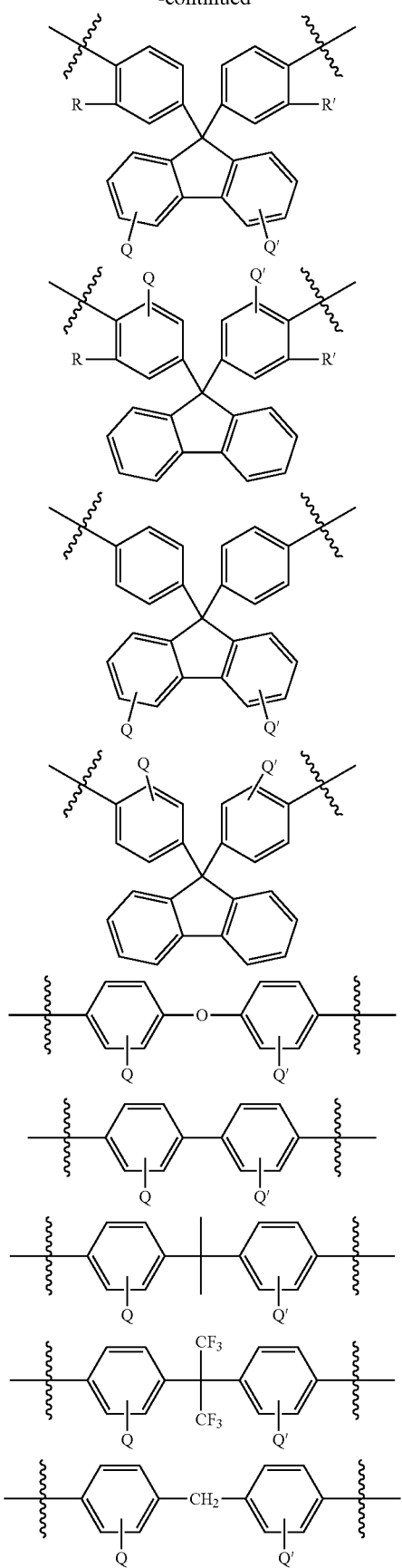
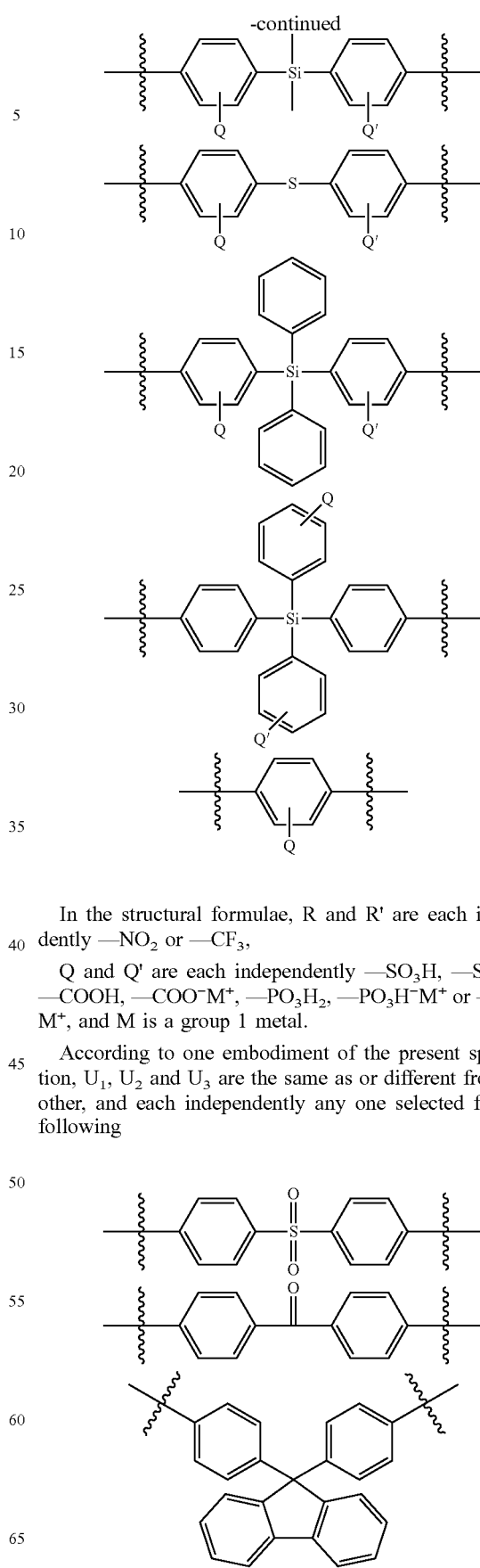

In the structural formulae, R and R' are each independently —NO$_2$ or —CF$_3$,

Q and Q' are each independently —SO$_3$H, —SO$_3^-$M$^+$, —COOH, —COO$^-$M$^+$, —PO$_3$H$_2$, —PO$_3$H$^-$M$^+$ or —PO$_3^{2-}$M$^+$, and M is a group 1 metal.

According to one embodiment of the present specification, U$_1$, U$_2$ and U$_3$ are the same as or different from each other, and each independently any one selected from the following

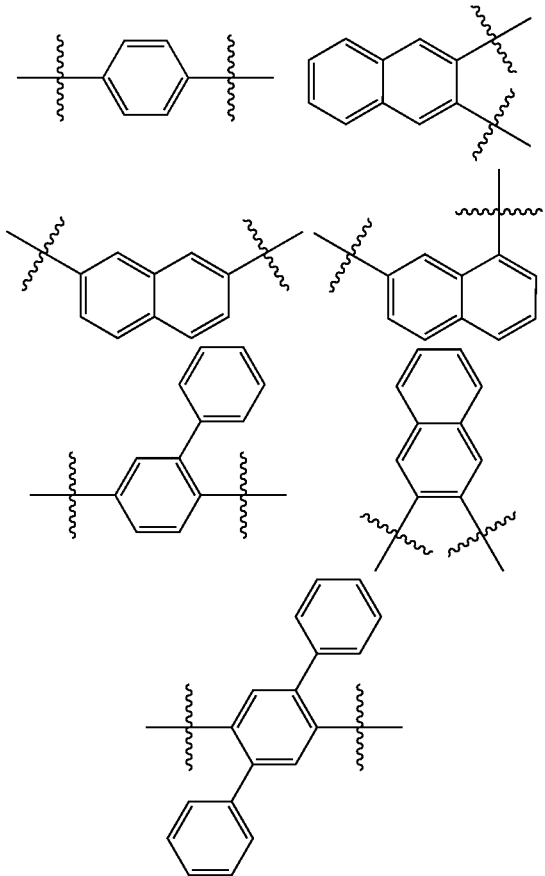

In the present specification,

means bonding with an adjacent substituent.

Examples of the substituents are described below, however, the substituents are not limited thereto.

In the present specification, the alkyl group may be linear or branched, and although not particularly limited thereto, the number of carbon atoms is preferably from 1 to 50. Specific examples thereof may include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be linear or branched, and although not particularly limited thereto, the number of carbon atoms is preferably from 2 to 50. Specific examples thereof preferably include aryl group-substituted alkenyl groups such as a stylbenyl group or a styrenyl group, but are not limited thereto.

In the present specification, the alkoxy group may be linear or branched, and although not particularly limited thereto, the number of carbon atoms is preferably from 1 to 50.

In the present specification, the cycloalkyl group is not particularly limited, but preferably has 3 to 60 carbon atoms, and particularly, a cyclopentyl group and a cyclohexyl group are preferred.

In the present specification, examples of the halogen group may include fluorine, chlorine, bromine or iodine.

In the present specification, the number of carbon atoms of the amine group is not particularly limited, but is preferably from 1 to 50. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the number of carbon atoms of the arylamine group is not particularly limited, but is preferably from 6 to 50. Examples of the arylamine group mean substituted or unsubstituted monocyclic diarylamine groups, substituted or unsubstituted multicyclic diarylamine groups or substituted or unsubstituted monocyclic and multicyclic diarylamine groups.

In the present specification, the aryl group may be monocyclic or multicyclic, and although not particularly limited thereto, the number of carbon atoms is preferably from 6 to 60. Examples of the aryl group may include monocyclic aromatic groups such as a phenyl group, a biphenyl group, a triphenyl group, a terphenyl group and a stilbene group, multicyclic aromatic groups such as a naphthyl group, a binaphthyl group, an anthracenyl group, a phenanthrenyl group, a pyrenyl group, a perylenyl group, a tetracenyl group, a chrysenyl group, a fluorenyl group, an acenaphthacenyl group, a triphenylene group and a fluoranthene group, and the like, however, the examples are not limited thereto.

In the present specification, the heteroaryl group includes S, O or N as a heteroatom, and although not particularly limited thereto, the number of carbon atoms is preferably from 2 to 60. Specific examples of the heteroaryl group may include a pyridyl group, a pyrrolyl group, a pyrimidyl group, a pyridazinyl group, a furanyl group, a thienyl group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, an acridinyl group, a phenanthridinyl group, an imidazopyridinyl group, a diazanaphthalenyl group, a triazaindene group, an indolyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a phenazinyl group and the like, or fused rings thereof, but are not limited thereto.

In the present specification, the fluorenyl group may be substituted with other substituents, and substituents may bond to each other to form a ring. Examples thereof may include

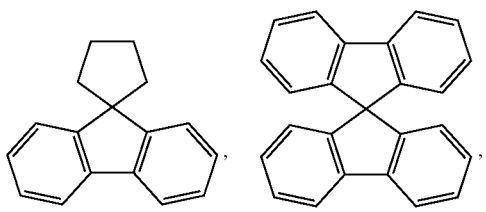

-continued

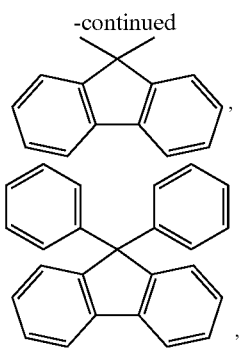

and the like.

In addition, in Chemical Formulae 2 to 7, the term "substituted or unsubstituted" means being substituted with one or more substituents selected from the group consisting of deuterium; a halogen group; an alkyl group; an alkenyl group; an alkoxy group; a cycloalkyl group; a silyl group; an arylalkenyl group; an aryl group; a boron group; an alkylamine group; an aralkylamine group; an arylamine group; a carbazole group; an arylamine group; an aryl group; a nitrile group; a nitro group; a hydroxyl group and a cyano group, or having no substituents.

According to one embodiment of the present specification, the group 1 element may be Li, Na or K.

According to another embodiment, a weight average molecular weight of the polymer may be greater than or equal to 500 and less than or equal to 5,000,000 (g/mol), specifically, greater than or equal to 10,000 and less than or equal to 2,000,000 (g/mol), and more specifically, greater than or equal to 50,000 and less than or equal to 1,000,000 (g/mol).

When the copolymer has a weight average molecular weight of greater than or equal to 500 and less than or equal to 5,000,000 (g/mol), mechanical properties of an electrolyte membrane do not decline, and proper polymer solubility is maintained, and as a result, the electrolyte membrane may be readily manufactured.

In one embodiment of the present specification, a polydispersity index (PDI) of the polymer may be greater than or equal to 1 and less than or equal to 6 (Mw/Mn), and specifically, may be greater than or equal to 1.5 and less than or equal to 4 (Mw/Mn).

One embodiment of the present specification provides a polymer electrolyte membrane including the polymer. The polymer electrolyte membrane may exhibit effects described above.

In the present specification, the "electrolyte membrane" includes, as a membrane capable of exchanging ions, a membrane, an ion-exchange membrane, an ion-transfer membrane, an ion-conductive membrane, a separator, an ion-exchange separator, an ion-transfer separator, an ion-conductive separator, an ion-exchange electrolyte membrane, an ion-transfer electrolyte membrane, an ion-conductive electrolyte membrane or the like.

The polymer electrolyte membrane according to the present specification may be prepared using materials and/or methods known in the art except that the polymer electrolyte membrane includes the monomer derived from the compound for a brancher represented by Chemical Formula 1.

According to one embodiment of the present specification, the polymer electrolyte membrane has ion conductivity of greater than or equal to 0.01 S/cm and less than or equal to 0.5 S/cm, and specifically, greater than or equal to 0.01 S/cm and less than or equal to 0.3 S/cm.

In one embodiment of the present specification, ion conductivity of the polymer electrolyte membrane may be measured under a humidity condition. A humidity condition in the present specification may mean relative humidity (RH) of 10% to 100%.

According to one embodiment of the present specification, the electrolyte membrane may have a thickness of 1 μm to 200 μm, and specifically 10 μm to 100 μm. When the electrolyte membrane has a thickness of 1 μm to 200 μm, electric short and electrolyte material cross over are reduced, and an excellent cation conductivity property may be exhibited.

One embodiment of the present specification provides a membrane-electrode assembly including a positive electrode; a negative electrode; and an electrolyte membrane provided between the positive electrode and the negative electrode, wherein the electrolyte membrane is the polymer electrolyte membrane according to one embodiment of the present specification.

The membrane-electrode assembly (MEA) means an assembly of electrodes (positive electrode and negative electrode) in which an electrochemical catalyst reaction of fuel and air occurs and a polymer membrane in which hydrogen ion transfer occurs, and is a single assembled unit in which electrodes (positive electrode and negative electrode) and an electrolyte membrane are adhered.

According to one embodiment of the present specification, the membrane-electrode assembly has a form of a catalyst layer of a positive electrode and a catalyst layer of a negative electrode being brought into contact with an electrolyte membrane, and may be prepared using common methods known in the art. As one example, the membrane-electrode assembly may be prepared through thermocompressing the positive electrode; the negative electrode; and the electrolyte membrane located between the positive electrode and the negative electrode at 100 to 400 while sticking these together.

The positive electrode may include a positive electrode catalyst layer and a positive electrode gas diffusion layer. The positive electrode gas diffusion layer may again include a positive electrode micropore layer and a positive electrode substrate.

The negative electrode may include a negative electrode catalyst layer and a negative electrode gas diffusion layer. The negative electrode gas diffusion layer may again include a negative electrode micropore layer and a negative electrode substrate.

In addition, one embodiment of the present specification provides a fuel cell including the membrane-electrode assembly. Specifically, one embodiment of the present specification provides a polymer electrolyte-type fuel cell including a stack including two or more of the membrane-electrode assemblies and a bipolar plate provided between the membrane-electrode assemblies; a fuel supplying unit supplying fuel to the stack; and an oxidizer supplying unit supplying an oxidizer to the stack.

The positive electrode catalyst layer is a place where an oxidation reaction of fuel occurs, and catalysts selected from the group consisting of platinum, ruthenium, osmium, platinum-ruthenium alloys, platinum-osmium alloys, platinum-palladium alloys and platinum-transition metal alloys may be preferably used.

The negative electrode catalyst layer is a place where a reduction reaction of an oxidizer occurs, and platinum or platinum-transition metal alloys may be preferably used as catalysts. The catalysts may be used as they are, or may be used while being supported on a carbon-based carrier.

The process of introducing the catalyst layer may be carried out using common methods known in the art, and for example, a catalyst ink may be directed coated on the electrolyte membrane, or a catalyst ink may be coated on the gas diffusion layer to form the catalyst layer. Herein, the coating method of the catalyst ink is not particularly limited, and methods of spray coating, tape casting, screen printing, blade coating, die coating, spin coating or the like may be used. The catalyst ink may be typically formed with a catalyst, a polymer ionomer and a solvent.

The gas diffusion layer becomes a migration path of reaction gases and water while performing a role of a current conductor, and has a porous structure. Accordingly, the gas diffusion layer may be formed including a conductive substrate. As the conductive substrate, carbon paper, carbon cloth or carbon felt may be preferably used.

In addition, the gas diffusion layer may be formed further including a micropore layer between the catalyst layer and the conductive substrate. The micropore layer may be used for enhancing fuel cell performance under a low humidity condition, and performs a role of allowing the electrolyte membrane to be under a sufficiently wet condition by having the amount of water escaping outside the gas diffusion layer being small.

When using the electrolyte membrane according to one embodiment of the present specification as an ion-exchange membrane of a fuel cell, effects described above may be exhibited. One embodiment of the present specification provides a polymer electrolyte-type fuel cell including two or more membrane-electrode assemblies; a stack including a bipolar plate provided between the membrane-electrode assemblies; a fuel supplying unit supplying fuel to the stack; and an oxidizer supplying unit supplying an oxidizer to the stack.

The fuel cell may be prepared through common methods known in the art using the membrane-electrode assembly according to one embodiment of the present specification. For example, the fuel cell may be prepared forming with the membrane-electrode assembly prepared above and a bipolar plate.

FIG. 3 is a schematic diagram showing a principle of electricity generation of a fuel cell, and in the fuel cell, a most basic unit generating electricity is a membrane-electrode assembly (MEA), and this is focused with an electrolyte membrane (100), and a positive electrode (200a) and a negative electrode (200b) formed on both sides of the electrolyte membrane (100). When referring to FIG. 3 showing a principle of electricity generation of a fuel cell, an oxidation reaction of fuel such as hydrogen or hydrocarbon such as methanol and butane occurs in the positive electrode (200a) to generate hydrogen ions ($H^+$) and electrons ($e^-$), and the hydrogen ions migrate to the negative electrode (200b) through the electrolyte membrane (100). In the negative electrode (200b), water is produced through the reaction of the hydrogen ions transferred through the electrolyte membrane (100), an oxidizer such oxygen, and electrons. Electrons migrate to an external circuit through such a reaction.

The fuel cell of the present specification includes a stack, a fuel supplying unit and an oxidizer supplying unit.

FIG. 5 is a diagram schematically illustrating the fuel cell, and the fuel cell is formed including a stack (60), an oxidizer supplying unit (70) and a fuel supplying unit (80).

The stack (60) includes one, two or more of the membrane-electrode assemblies described above, and when two or more of the membrane-electrode assemblies are included, a separator provided therebetween is included. The separator prevents the membrane-electrode assemblies from being electrically connected, and performs a role of transferring fuel and oxidizer supplied from the outside to the membrane-electrode assemblies.

The oxidizer supplying unit (70) performs a role of supplying an oxidizer to the stack (60). As the oxidizer, oxygen is typically used, and oxygen or air may be injected with a pump (70) to be used.

The fuel supplying unit (80) performs a role supplying fuel to the stack (60), and may be formed with a fuel tank (81) storing fuel and a pump (82) supplying the fuel stored in the fuel tank (81) to the stack (60). As the fuel, hydrogen or hydrocarbon fuel in a gas or liquid state may be used. Examples of the hydrocarbon fuel may include methanol, ethanol, propanol, butanol or natural gas.

The fuel cell may include a polymer electrolyte fuel cell, a direct liquid fuel cell, a direct methanol fuel cell, a direct formic acid fuel cell, a direct ethanol fuel cell, a direct dimethyl ether fuel cell or the like.

One embodiment of the present specification also provides a redox flow battery including the polymer electrolyte membrane. Specifically, one embodiment of the present specification provides a redox flow battery including a cell including a positive electrode and a positive electrode liquid electrolyte; a negative electrode cell including a negative electrode and a negative electrode liquid electrolyte; and the polymer electrolyte membrane according to one embodiment of the present specification provided between the positive electrode cell and the negative electrode cell.

When using the electrolyte membrane according to one embodiment of the present specification as an ion-exchange membrane of the redox flow battery, effects described above may be exhibited.

The redox flow battery may be prepared using common methods known in the art except that the redox flow battery includes the polymer electrolyte membrane according to one embodiment of the present specification.

As illustrated in FIG. 4, the redox flow battery is divided into a positive electrode cell (32) and a negative electrode cell (33) by an electrolyte membrane (31). The positive electrode cell (32) and the negative electrode cell (33) include a positive electrode and a negative electrode, respectively. The positive electrode cell (32) is connected to a positive electrode tank (10) for supplying and releasing a positive electrode liquid electrolyte (41) through a pipe. The negative electrode cell (33) is also connected to a negative electrode tank (20) for supplying and releasing a negative electrode liquid electrolyte (42) through a pipe. The liquid electrolytes circulate through pumps (11, 21), and through an oxidation/reduction reaction (that is, a redox reaction) changing the oxidation number of ions, charge and discharge occur in the positive electrode and the negative electrode.

Hereinafter, the present specification will be described in more detail with reference to examples. However, the following examples are for illustrative purposes only, and the scope of the present specification is not limited thereto.

POLYMER SYNTHESIS EXAMPLE 1

1) Synthesis of Polymer 1-A

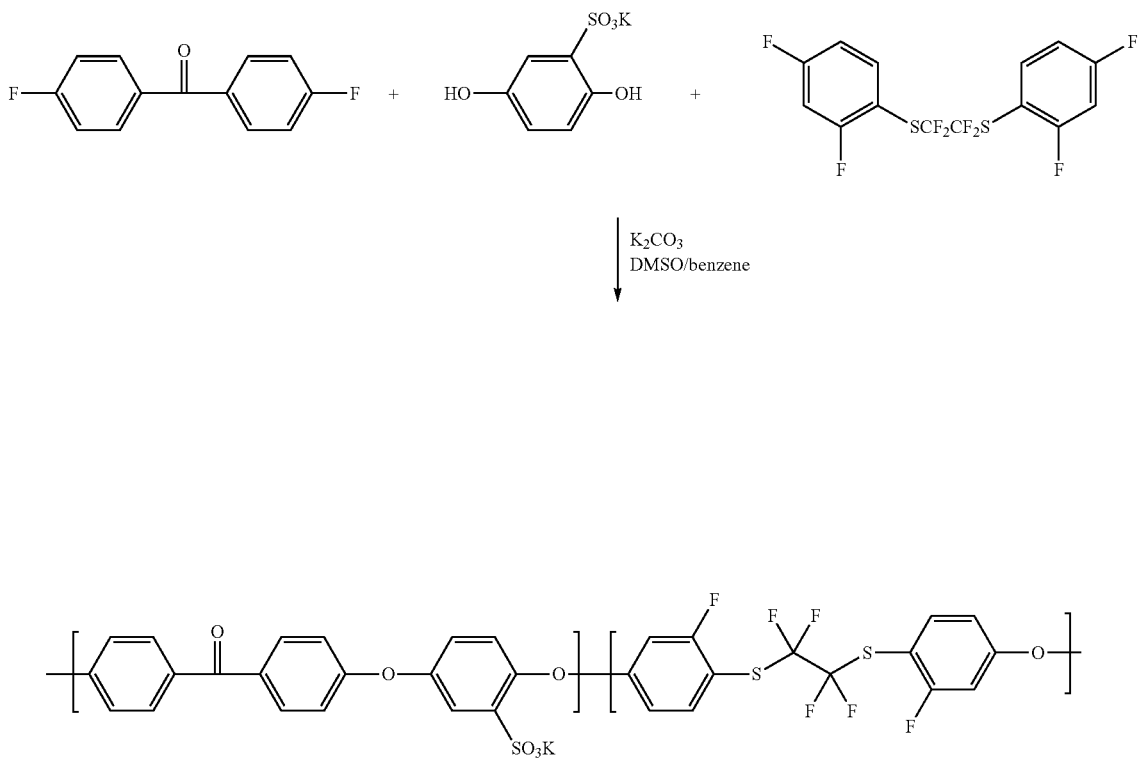

[Polymer 1-A]

After preparing a mixture by placing 11.35 g (0.1040 mol) of bis(4-fluorophenyl)methanone, 12.5 g (0.1095 mol) of potassium hydroquinonesulfonate, 13.6 g (0.1971 mol) of $K_2CO_3$, 0.9328 g of 1,2-bis((2,4-difluorophenyl)thio)-1,1,2,2-tetrafluoroethane, 119.25 g of dimethyl sulfoxide (DMSO) and 119.25 g of benzene in a 500 ml double jacket, the result was heated for 5 hours at 140° C. under nitrogen atmosphere, and after completely removing an azeotrope adsorbed to molecular sieves of a Dean-Stark apparatus as benzene flowed backward with pressurized nitrogen, polymerization was carried out for 20 hours at 180° C.

2) Synthesis of Polymer 1-B

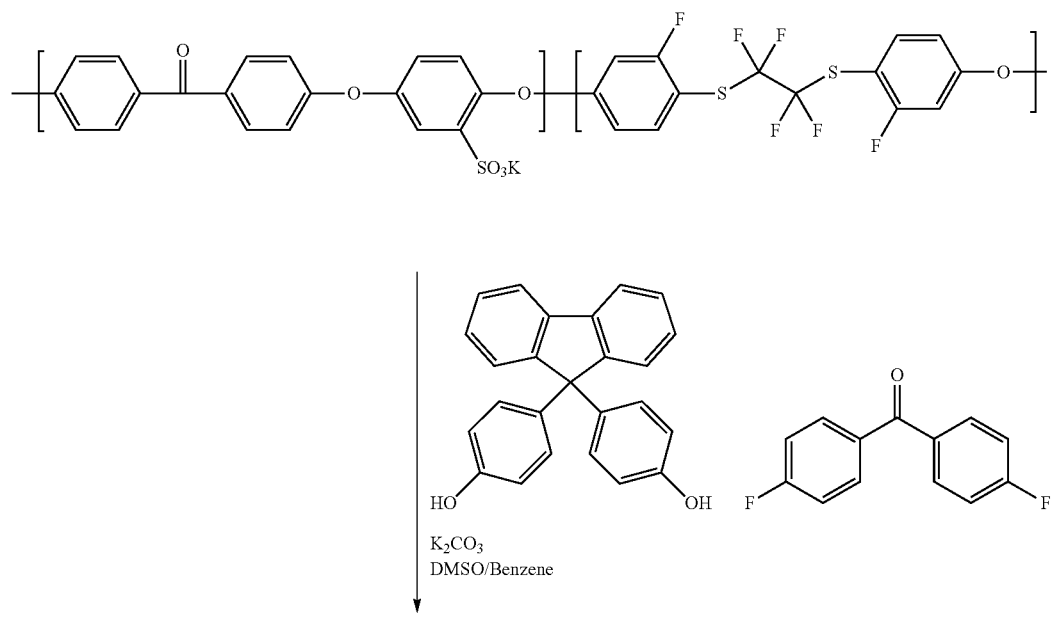

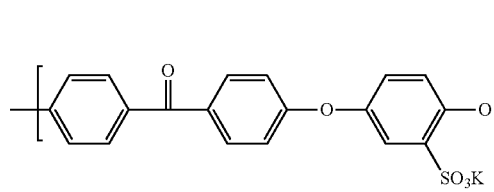

-continued

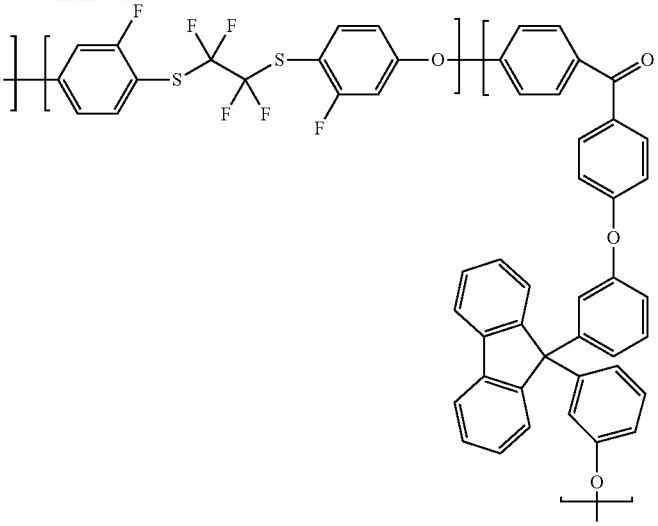

[Polymer 1-B]

After cooling the mixture including Polymer 1-A to room temperature, a mixture was prepared by placing 1.691 g (0.1877 mol) of bis(4-fluorophenyl)methanone, 3.543 g (0.2033 mol) of 9,9-bis(4-hydroxyphenyl)fluorene, 0.0069 g of 1,2-bis((2,4-difluorophenyl)thio)-1,1,2,2-tetrafluoroethane, 19.4 g (0.2816 mol) of $K_2CO_3$, 34.53 g of dimethyl sulfoxide (DMSO) and 34.53 g of benzene, and then the result was heated for 5 hours at 140° C. under nitrogen atmosphere, and after completely removing an azeotrope adsorbed to molecular sieves of a Dean-Stark apparatus as benzene flowed backward with pressurized nitrogen, the benzene in the Dean-Stark was discharged after reflux, and polymerization was carried out for 20 hours at 180° C. in dimethyl sulfoxide (DMSO).

Subsequently, after cooling the result to room temperature, the polymerized polymer was sunk in 3 L of isopropyl alcohol to faun precipitates, and then the solvent of the precipitates was removed, the result was washed for 48 hours at room temperature using deionized water to remove residual $K_2CO_3$, and then dried for 48 hours in a 90° C. vacuum oven to obtain a polymer introducing a partial fluorine-based brancher including Polymer 1-B.

3) Final Polymer Yield

The polymerized polymer was acid treated for 24 hours in a 10 wt %(/wt) aqueous sulfuric acid solution at 80° C., and then washed 10 times or more using deionized water, and after that, the result was dried for 48 hours in a 90° C. vacuum oven to obtain a final polymer introducing a partial fluorine-based brancher.

COMPARATIVE SYNTHESIS EXAMPLE 1

An experiment was carried out in the same manner as in Example 1 except that the following Compound Z was used as the brancher instead of 1,2-bis((2,4-difluorophenyl)thio)-1,1,2,2-tetrafluoroethane.

[Compound Z]

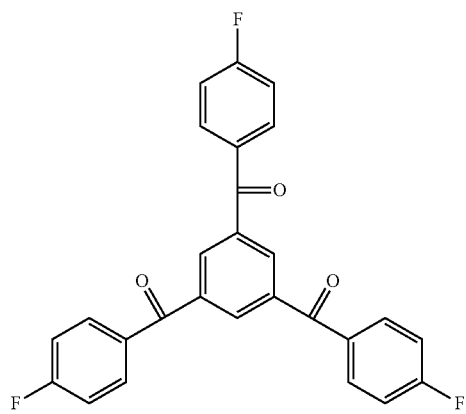

A graph of an NMR analysis result for the compound for a brancher represented by Chemical Formula 1 prepared according to the above-mentioned reaction formula (H-NMR in DMSO-d6, 500 MHz) is shown in FIG. 1. In addition, an NMR analysis result for the carbons corresponding to the following (a), (b) and (c) is shown in more detail in FIG. 2.

TEST EXAMPLE (FENTON'S TEST)

A polymer electrolyte membrane made to a membrane using the polymer (Polymer 1) synthesized in Synthesis Example 1 was placed in a 3% $H_2O_2$ solution including a small amount of $Fe^{2+}$ ions, and the result was stirred for 20 hours at 80° C., and then stability of the polymer membrane was measured by measuring $F^-$ ions included in the solution.

COMPARATIVE TEST EXAMPLE

A test was carried out in the same manner as in the test example, except that a polymer electrolyte membrane using Compound Z as the brancher instead of Polymer 1 was used.

TABLE 1

| Type of Electrolyte Membrane | Composition of Fenton Reagent | Temperature (° C.) | Weight Average Molecular Weight (g/mol) | Ion-Exchange Capacity (meq/g) | Decomposition Efficiency (%) |
|---|---|---|---|---|---|
| Test Example | 3% $H_2O_2$/4 ppm $Fe^{2+}$ Solution | 80 | 443,500 | 1.84 | 4% to 6% |
| Comparative Test Example | | | 367,000 | 1.82 | 8% to 10% |

It was seen that the polymer electrolyte membrane made to a membrane using the polymer of the present disclosure had a higher ion-exchange capacity value and lower decomposition efficiency for Fenton reagent compared to the polymer electrolyte membrane of the Comparative Test Example using an existing brancher.

The invention claimed is:

1. A polymer, comprising a unit derived from a compound for a brancher represented by the following Chemical Formula 1, wherein the unit derived from the compound for a brancher is included in greater than or equal to 0.001% by weight and less than or equal to 10% by weight with respect to a total weight of the polymer:

[Chemical Formula 1]

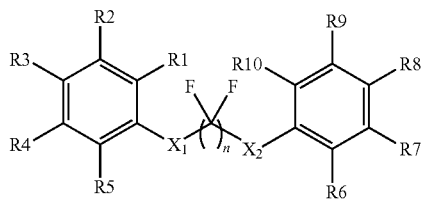

wherein, in Chemical Formula 1,

R1 to R10 are the same as or different from each other, and each independently hydrogen or a halogen group;

two of R1 to R5 are a halogen group;

two of R6 to R10 are a halogen group;

$X_1$ and $X_2$ are the same as or different from each other, and each independently NR, O, S or $SO_2$;

R is hydrogen; deuterium; or a substituted or unsubstituted alkyl group; and n is an integer of 1 to 6.

2. The polymer of claim 1, wherein the halogen group in Chemical Formula 1 is fluorine or chlorine.

3. The polymer of claim 1, wherein R3, R5, R6 and R8 in Chemical Formula 1 are a halogen group.

4. The polymer of claim 1, wherein n in Chemical Formula 1 is 2 or more.

5. The polymer of claim 1, wherein $X_1$ and $X_2$ in Chemical Formula 1 are the same as or different from each other, and each independently S or $SO_2$.

6. The polymer of claim 1, wherein the compound for a brancher represented by Chemical Formula 1 is any one selected from the following structures:

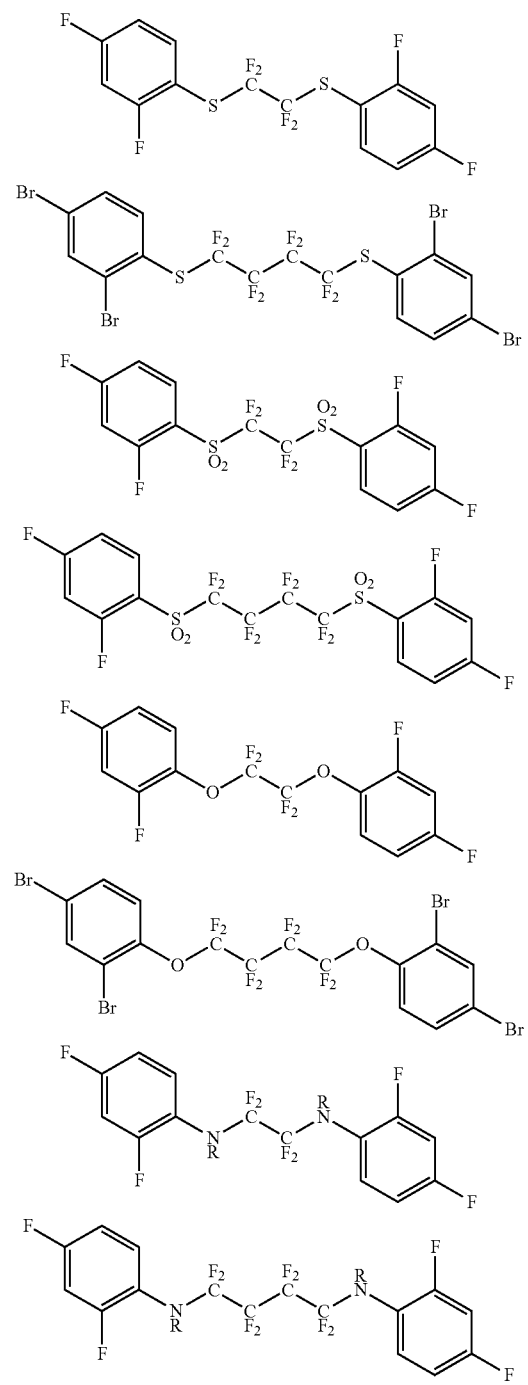

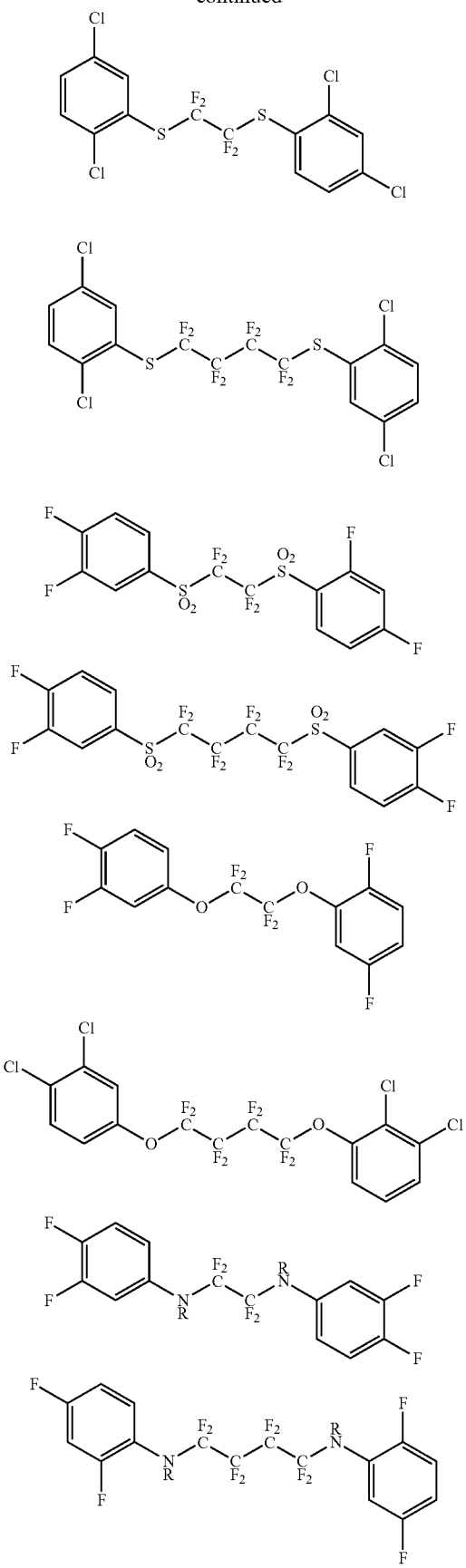
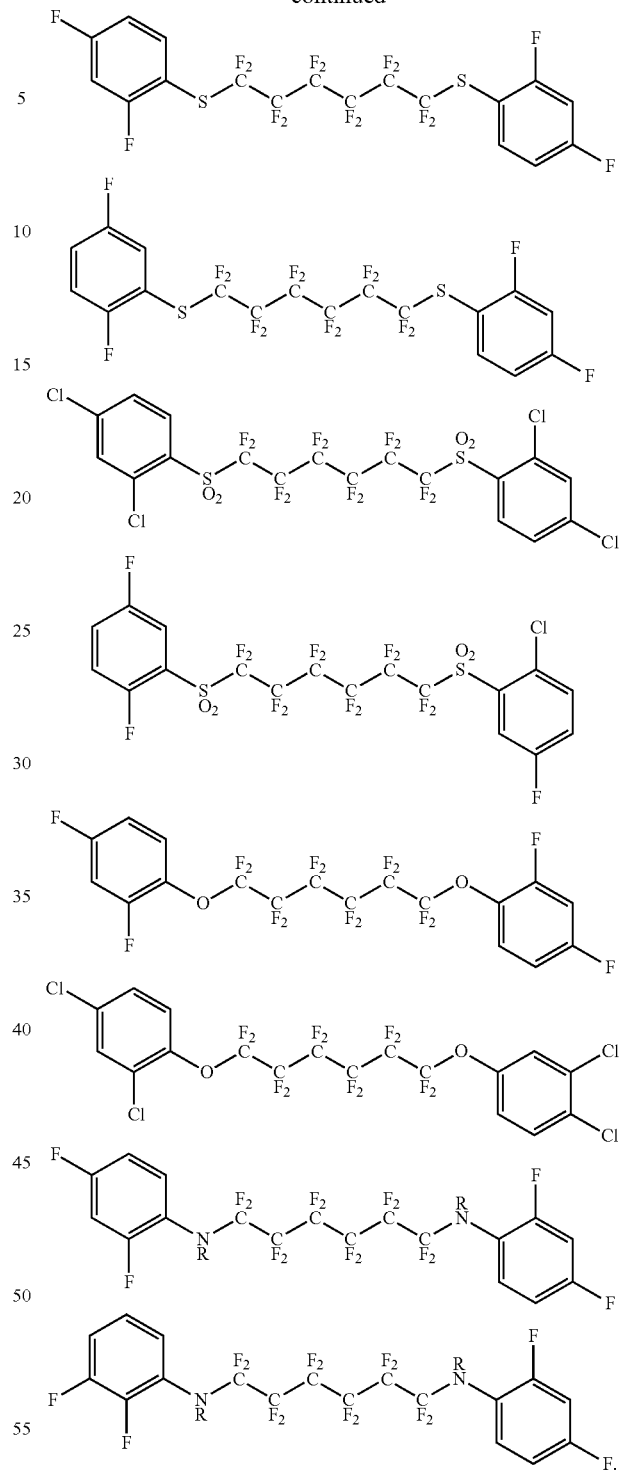

7. The polymer of claim 1, which is a block-type copolymer including hydrophilic blocks and hydrophobic blocks.

8. The polymer of claim 1, wherein the unit derived from the compound for a brancher is located between the hydrophilic blocks, between the hydrophobic blocks or between the hydrophilic block and the hydrophobic block.

9. The polymer of claim 1, which has a weight average molecular weight of greater than or equal to 500 and less than or equal to 5,000,000 (g/mol).

10. The polymer of claim 1, which has a polydispersity index (PDI) of greater than or equal to 1 and less than or equal to 6 (Mw/Mn).

11. A polymer electrolyte membrane comprising the polymer of claim 1.

12. The polymer electrolyte membrane of claim 11, which has ion conductivity of greater than or equal to 0.01 S/cm and less than or equal to 0.5 S/cm.

13. A membrane-electrode assembly comprising:
a positive electrode;
a negative electrode; and
an electrolyte membrane provided between the positive electrode and the negative electrode,
wherein the electrolyte membrane is the polymer electrolyte membrane of claim 11.

14. A polymer electrolyte-type fuel cell comprising:
a stack including two or more of the membrane-electrode assemblies of claim 13 and a bipolar plate provided between the membrane-electrode assemblies;
a fuel supplying unit supplying fuel to the stack; and
an oxidizer supplying unit supplying an oxidizer to the stack.

15. A redox flow battery comprising:
a positive electrode cell including a positive electrode and a positive electrode liquid electrolyte;
a negative electrode cell including a negative electrode and a negative electrode liquid electrolyte; and
the polymer electrolyte membrane of claim 11 provided between the positive electrode cell and the negative electrode cell.

16. The polymer of claim 1, wherein the unit derived from the compound for a brancher is one of the following units:

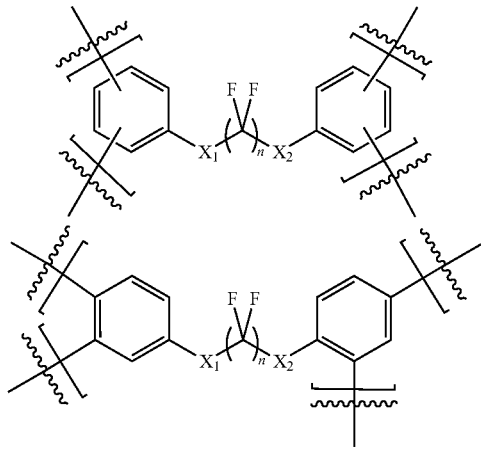

-continued

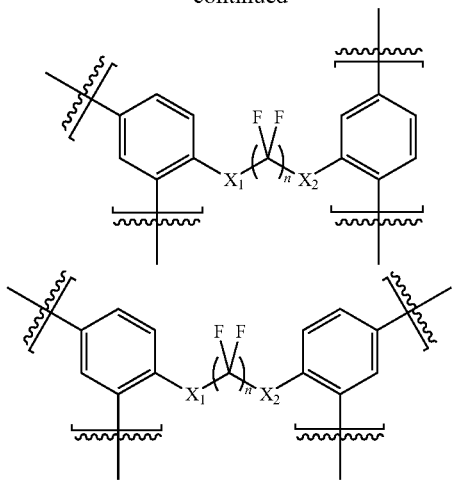

17. A polymer, comprising a unit derived from a compound for a brancher represented by the following Chemical Formula 1,
wherein the unit derived from the compound for a brancher is included in greater than or equal to 0.001% by weight and less than or equal to 10% by weight with respect to a total weight of the polymer:

[Chemical Formual 1]

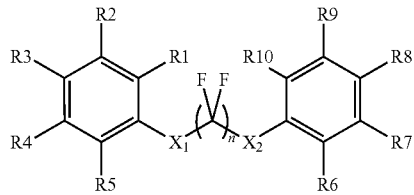

wherein, in Chemical Formula 1,
R3, R5, R6 and R8 are the same as or different from each other, and each independently a halogen group, and R1, R2, R4, R7, R9 and R10 are a hydrogen;
$X_1$ and $X_2$ are the same as or different from each other, and each independently NR, O, S or $SO_2$;
R is hydrogen; deuterium; or a substituted or unsubstituted alkyl group; and
n is an integer of 1 to 6.

* * * * *